United States Patent [19]
Alfano et al.

[11] Patent Number: 5,719,399
[45] Date of Patent: Feb. 17, 1998

[54] IMAGING AND CHARACTERIZATION OF TISSUE BASED UPON THE PRESERVATION OF POLARIZED LIGHT TRANSMITTED THERETHROUGH

[75] Inventors: Robert R. Alfano, Bronx; Stavros G. Demos, Astoria, both of N.Y.

[73] Assignee: The Research Foundation of City College of New York, New York, N.Y.

[21] Appl. No.: 573,939

[22] Filed: Dec. 18, 1995

[51] Int. Cl.$^6$ .................................................. G01N 21/49
[52] U.S. Cl. ............................... 250/341.3; 128/664
[58] Field of Search ........................ 250/341.3, 341.1, 250/358.1; 128/664, 665

[56] References Cited

U.S. PATENT DOCUMENTS

| | | | |
|---|---|---|---|
| 4,945,239 | 7/1990 | Wist et al. | 250/358.1 |
| 5,371,368 | 12/1994 | Alfano et al. | 250/341.1 |

OTHER PUBLICATIONS

Patterson et al., "Absorption spectroscopy in tissue–simulating materials: a theoretical and experimental study of photon paths," Applied Optics, 34(1):22–30 (Jan. 1, 1995).

Tsuchiya et al., "Photon Migration for Turbid Biological Medium Having Various Shapes," Jpn. J. Appl. Phys., 34:L79–81 (Jan. 1, 1995).

Primary Examiner—David P. Porta
Assistant Examiner—Richard Hanig
Attorney, Agent, or Firm—Kriegsman & Kriegsman

[57] ABSTRACT

A method and apparatus for imaging and/or characterizing a tissue based upon the extent to which initially polarized light maintains its polarization after propagating through the tissue. In a preferred embodiment, the present invention relates to a method for identifying a tissue in question, the method comprising the steps of: (a) illuminating the tissue with a pulse of light, the pulse of light being polarized and having an initial state of polarization, whereby light consisting of a ballistic component, a snake-like component and a diffuse component emerges from the illuminated tissue; (b) passing the emergent light from the illuminated tissue through one of a polarizer oriented parallel to the initial state of polarization of the pulse of light and an analyzer oriented perpendicular to the initial state of polarization of the pulse of light; (c) detecting the light passed through one of the polarizer and the analyzer; and (d) comparing the detected light to appropriate standards so as to identify the type of tissue tested, i.e., breast and brain for optical mammography and tomography.

62 Claims, 23 Drawing Sheets

IMAGING AND CHARACTERIZATION OF TISSUE BASED UPON THE PRESERVATION OF POLARIZED LIGHT TRANSMITTED THERETHROUGH

BACKGROUND OF THE INVENTION

The present invention relates generally to methods for imaging objects located in or behind turbid media and more particularly to a novel method for imaging objects in or behind turbid media.

As can readily be appreciated, there are many situations in which the detection of an object present in a turbid, i.e., highly scattering, medium is highly desirable. For instance, the detection of a tumor embedded within a tissue is one such example. Although X-ray techniques do provide some measure of success in detecting objects in turbid media, they are not typically well-suited for detecting very small objects, e.g., tumors less than 1 mm in size embedded in tissues, or for detecting objects in thick media. In addition, X-ray radiation can present safety hazards to a person exposed thereto. Ultrasound and magnetic resonance imaging (MRI) offer alternatives to the use of X-rays but have their own drawbacks.

Another technique used to detect objects in turbid media, such as tumors in tissues, is transillumination. In transillumination, visible light is incident on one side of a medium and the light emergent from the opposite side of the medium is used to form an image. Objects embedded in the medium typically absorb the incident light and appear in the image as shadows. Unfortunately, the usefulness of transillumination as a detection technique is severely limited in those instances in which the medium is thick or the object is very small. This is because light scattering within the medium contributes to noise and reduces the intensity of the unscattered light used to form the image shadow.

To improve the detectability of small objects located in a turbid medium using transillumination, many investigators have attempted to selectively use only certain components of the transilluminating light signal. This may be done by exploiting the properties of photon migration through a scattering medium. Photons migrating through a turbid medium have traditionally been categorized into three major signal components: (1) the ballistic (coherent) photons which arrive first by traveling over the shortest, most direct path; (2) the snake (quasi-coherent) photons which arrive within the first δt after the ballistic photons and which deviate, only to a very slight extent, off a straight-line propagation path; and (3) the diffusive (incoherent) photons which experience comparatively more scattering than do ballistic and snake photons and, therefore, deviate more considerably from the straight-line propagation path followed by ballistic and snake photons.

Because it has been believed that ballistic and snake photons contain the least distorted image information and that diffusive photons lose most of the image information, efforts to make transillumination work most effectively with turbid media have focused on techniques which permit the selective detection of ballistic and snake photons while rejecting diffusive photons. This process of selection and rejection have been implemented in various time-gating, space-gating and time/space-gating techniques. Patents, patent applications and publications which disclose certain of these techniques include U.S. Pat. No. 5,140,463, inventors Yoo et al., which issued Aug. 18, 1992; U.S. Pat. No. 5,143,372, inventors Alfano et al., which issued Aug. 25, 1992; U.S. Pat. No. 5,227,912, inventors Ho et al., which issued Jul. 13, 1993; presently-pending and allowed U.S. patent application Ser. No. 07/920,193, inventors Alfano et al., filed Jul. 23, 1992; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); Wang et al., "Kerr-Fourier imaging of hidden objects in thick turbid media," *Optics Letters*, Vol. 18, No. 3, pp. 241–243 (Feb. 1, 1993); Yoo et al., "Time-resolved coherent and incoherent components of forward light scattering in random media," *Optics Letters*, Vol. 15, No. 6, pp. 320–322 (Mar. 15, 1990); Chen et al., "Two-dimensional imaging through diffusing media using 150-fs gated electronic holography techniques," *Optics Letters*, Vol. 16, No. 7, pp. 487–489 (Apr. 1, 1991); Duncan et al., "Time-gated imaging through scattering media using stimulated Raman amplification," *Optics Letters*, Vol. 16, No. 23, pp. 1868–1870 (Dec. 1, 1991), all of which are incorporated herein by reference.

Of the above-listed art, Wang et al., "Kerr-Fourier imaging of hidden objects in thick turbid media," *Optics Letters*, Vol. 18, No. 3, pp. 241–243 (Feb. 1, 1993) is illustrative. In this article, there is disclosed a time/space-gating system for use in imaging opaque test bars hidden inside a 5.5 cm-thick 2.5% Intralipid solution. The disclosed system includes three main parts: a laser source, an optical Kerr gate and a detector. The laser source is a picosecond mode-locked laser system, which emits a 1054 nm, 8 ps laser pulse train as the illumination source. The second harmonic of the pulse train, which is generated by transmission through a potassium dihydrate phosphate (KDP) crystal, is used as the gating source. The illumination source is sent through a variable time-delay and is then used to transilluminate, from one side, the turbid medium containing the opaque object. The signal from the turbid medium located at the front focal plane of a lens is collected and transformed to a Kerr cell located at its back focal plane (i.e., the Fourier-transform spectral plane of a 4F system). That portion of the Kerr cell located at the focal point of the 4F system is gated at the appropriate time using the gating source so that only the ballistic and snake components are permitted to pass therethrough. The spatial-filtered and temporal-segmented signal is then imaged by a second lens onto a CCD camera.

Where, for example, the object located in the turbid medium is a tumor embedded within a tissue, one drawback common to all of the techniques described above is that none of these techniques affords one with the capability of characterizing the detected tumor as a malignant tumor or as a benign tumor, as the case may be.

SUMMARY OF THE INVENTION

It is an object of the present invention to provide a novel method for imaging an object located in or behind a turbid medium.

It is another object of the present invention to provide a method for imaging an object located in or behind a turbid medium that overcomes at least some of the drawbacks associated with existing methods for imaging objects located in or behind turbid media.

It is yet another object of the present invention to provide a complementary technique that includes time and spatial gating to enhance image information and clarity.

According to one aspect, the present invention relates to a method for imaging an object located in or behind a turbid medium, said method comprising the steps of: (a) illuminating the object through the turbid medium with a pulse of light, the pulse of light being polarized and having an initial state of polarization, whereby light consisting of a ballistic component, a snake-like component and a diffuse component emerges from the illuminated turbid medium; (b) passing the emergent light from the illuminated turbid medium through polarizing means oriented parallel to the initial state of polarization of said pulse of light to preferentially select said ballistic component and said snake-like component; and (c) forming an image of the light passed through said polarizing means.

According to another aspect, the present invention relates to a method for imaging an object located in or behind a turbid medium, said method comprising the steps of: (a) illuminating the object through the turbid medium with a pulse of light, the pulse of light being polarized and having an initial state of polarization, whereby light consisting of a ballistic component, a snake-like component and a diffuse component emerges from the illuminated turbid medium; (b) passing the emergent light from the illuminated turbid medium through an analyzer oriented perpendicular to the initial state of polarization of said pulse of light; and (c) forming an image of the light passed through said analyzer.

According to yet another aspect, the present invention relates to a method for imaging an object located in or behind a turbid medium, said method comprising the steps of: (a) illuminating the object through the turbid medium with a first pulse of light, the first pulse of light being polarized and having an initial state of polarization, whereby light from the first pulse consisting of a ballistic component, a snake-like component and a diffuse component emerges from the illuminated turbid medium; (b) passing the light from the first pulse emergent from the illuminated turbid medium through one of a polarizer oriented parallel to the initial state of polarization of said first pulse of light and an analyzer oriented perpendicular to the inital state of polarization of said first pulse of light; (c) detecting the light from the first pulse passed through one of said polarizer and said analyzer; (d) illuminating the object through the turbid medium with a second pulse of light, the second pulse of light being polarized in an initial state parallel to that of said first pulse of light, whereby light from the second pulse consisting of a ballistic component, a snake-like component and a diffuse component emerges from the illuminated turbid medium; (e) passing the light from the second pulse emergent from the illuminated turbid medium through the other of said polarizer and said analyzer; (f) detecting the light from the second pulse passed through the other of said polarizer and said analyzer; and (g) forming an image of the object in or behind the turbid medium using the light detected in steps (c) and (f).

The polarizer and analyzer of the aforementioned method may represent two distinct physical objects or may represent a single polarizer or a single analyzer that is arranged to serve either as a polarizer or as an analyzer, depending on its orientation.

According to still another aspect, the present invention relates to a method for imaging an object located in or behind a turbid medium, said method comprising the steps of: (a) illuminating the object through the turbid medium with a pulse of light, the pulse of light being polarized and having an initial state of polarization, whereby light from the pulse consisting of a ballistic component, a snake-like component and a diffuse component emerges from the illuminated turbid medium; (b) using a polarizing beamsplitter to split the light from the pulse emergent from the illuminated turbid medium into a first component having a state of polarization parallel to the initial state of polarization of the first pulse and a second component having a state of polarization perpendicular to the initial state of polarization of the first pulse; (c) detecting the first component; (d) detecting the second component; and (e) forming an image of the object in or behind the turbid medium using the light detected in steps (c) and (d).

According to still yet another aspect, the present invention relates to a method for identifying a tissue, said method comprising the steps of: (a) illuminating the tissue with a pulse of light, the pulse of light being polarized and having an initial state of polarization, whereby light consisting of a ballistic component, a snake-like component and a diffuse component emerges from the illuminated tissue; (b) passing the emergent light from the illuminated tissue through one of a polarizer oriented parallel to the initial state of polarization of said pulse of light and an analyzer oriented perpendicular to the initial state of polarization of said pulse of light; (c) detecting the light passed through one of said polarizer and said analyzer; and (d) comparing the detected light to appropriate standards so as to identify the type of tissue tested.

The methods described above may be repeated for one or more additional light pulses having wavelengths different from the first or initial pulse of light.

According to a further aspect, the present invention relates to an apparatus for imaging an object in a turbid medium, the apparatus comprising: (a) means for illuminating an object in a turbid medium from a first side thereof with a pulse of light, said pulse of light being polarized and having an initial state of polarization, whereby light consisting of a ballistic component, a snake-like component and a diffuse component emerges from the turbid medium; (b) polarization means for selectively passing the light emergent from the turbid medium based upon its polarization; (c) means for temporally resolving light passed through said polarization means; and (d) means for detecting the temporally resolved light.

Additional objects, features, aspects and advantages of the present invention will be set forth in part in the description which follows, and in part will be obvious from the description or may be learned by practice of the invention. Various embodiments of the invention will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

$$D(\lambda, t) = \frac{I(\lambda, t)_{parallel} - I(\lambda, t)_{perpendicular}}{I(\lambda, t)_{parallel} + I(\lambda, t)_{perpendicular}} .$$

Figure 6:
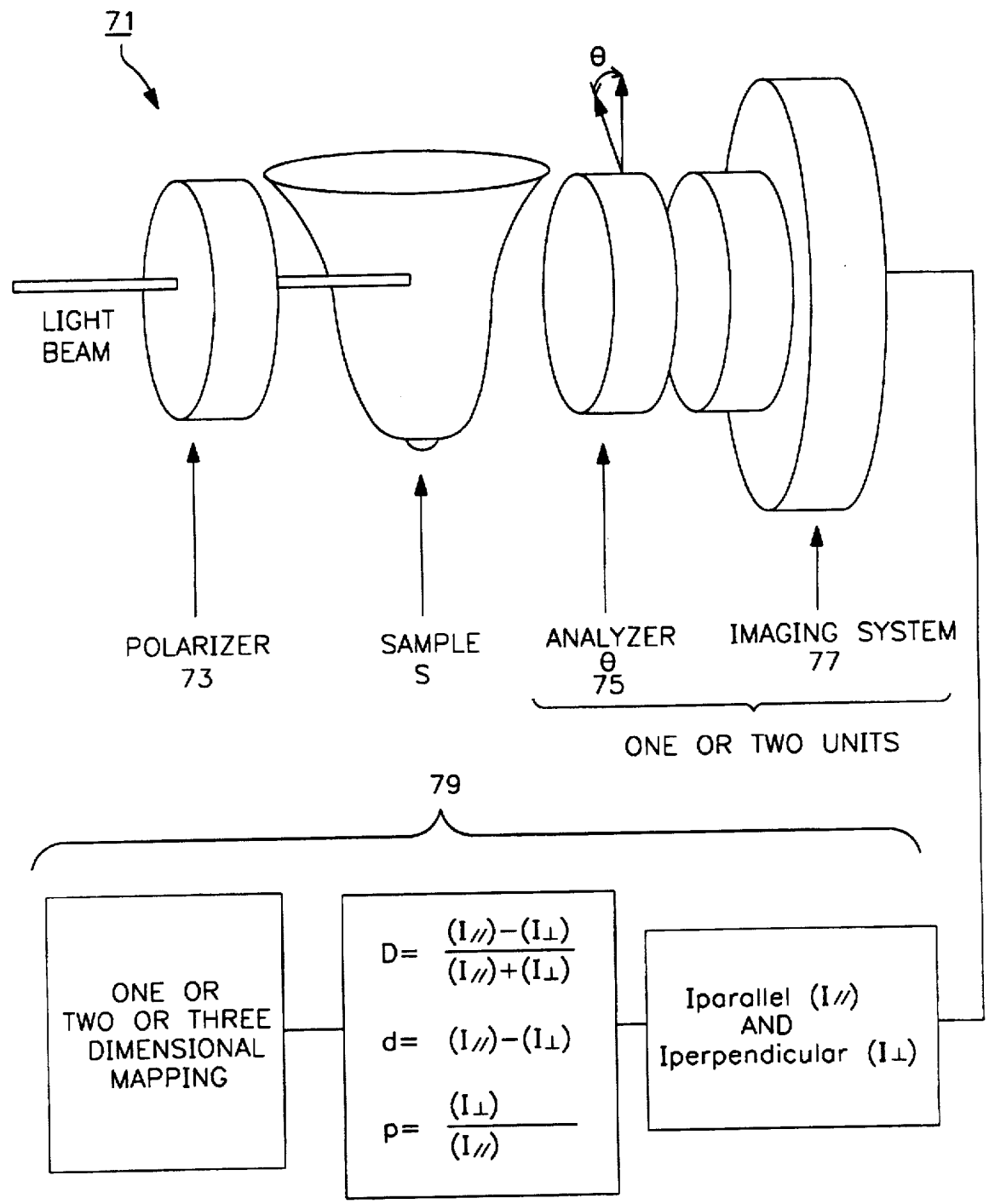
Figure 7:
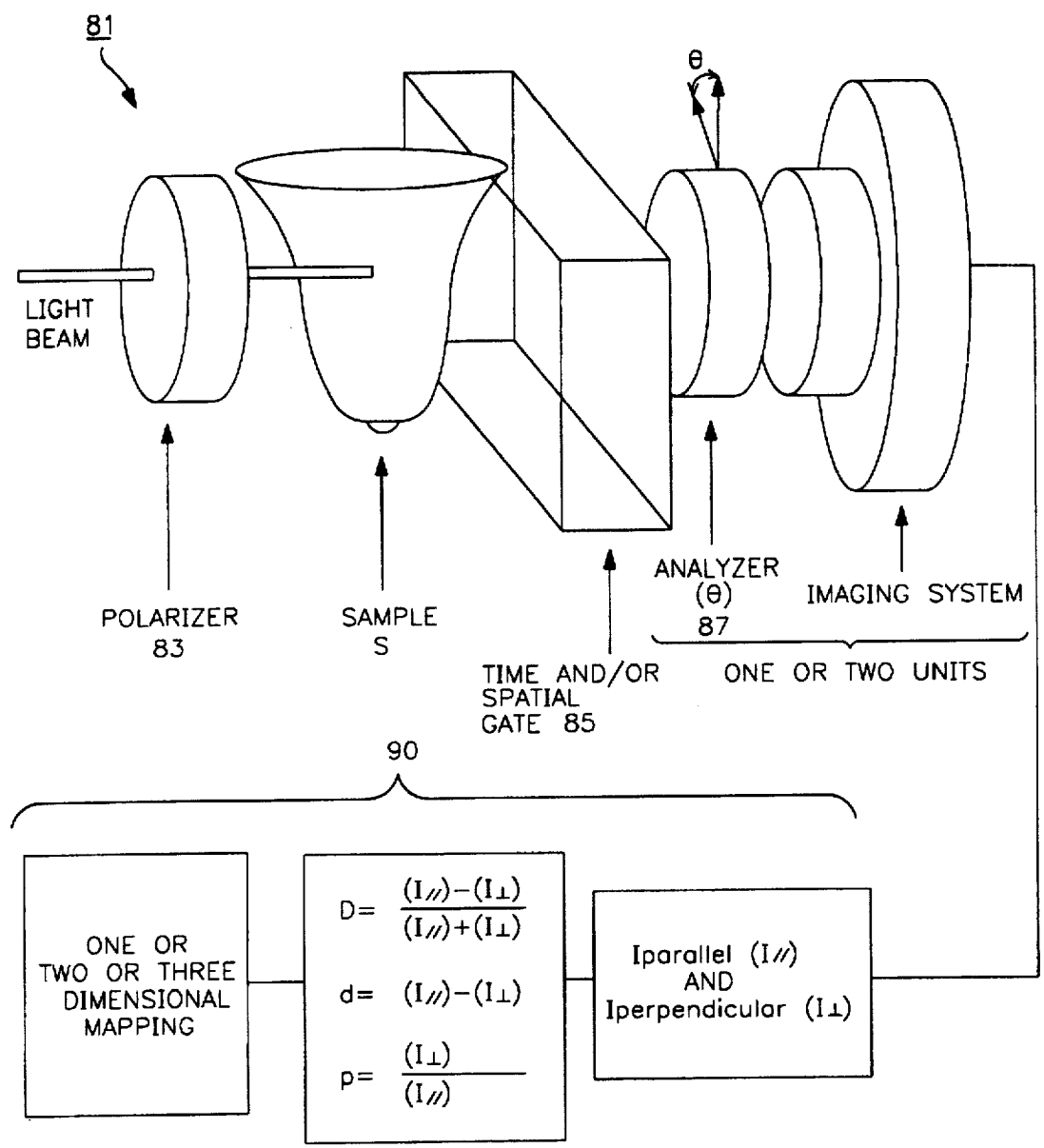
Figure 8:
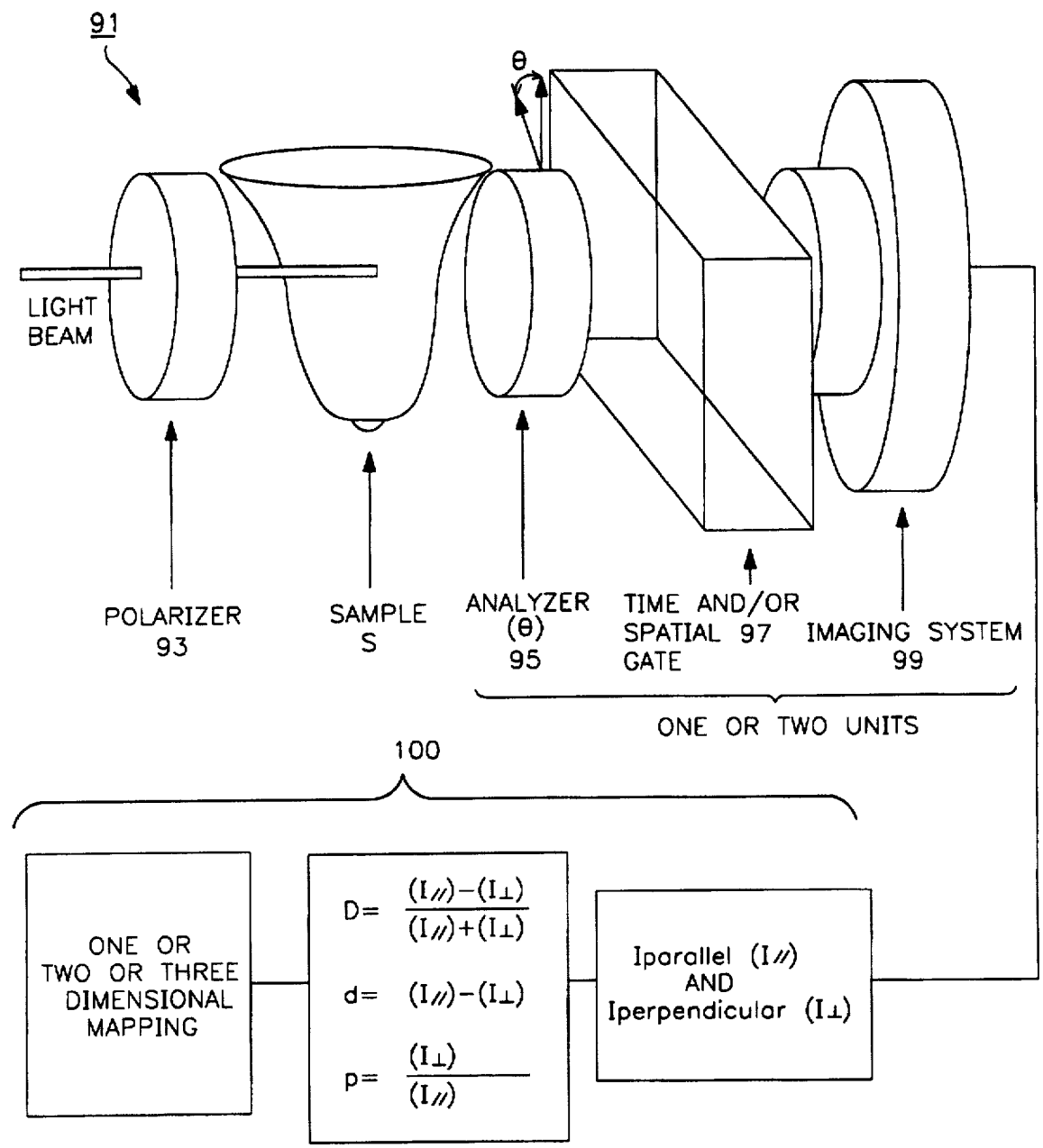
Figure 9:
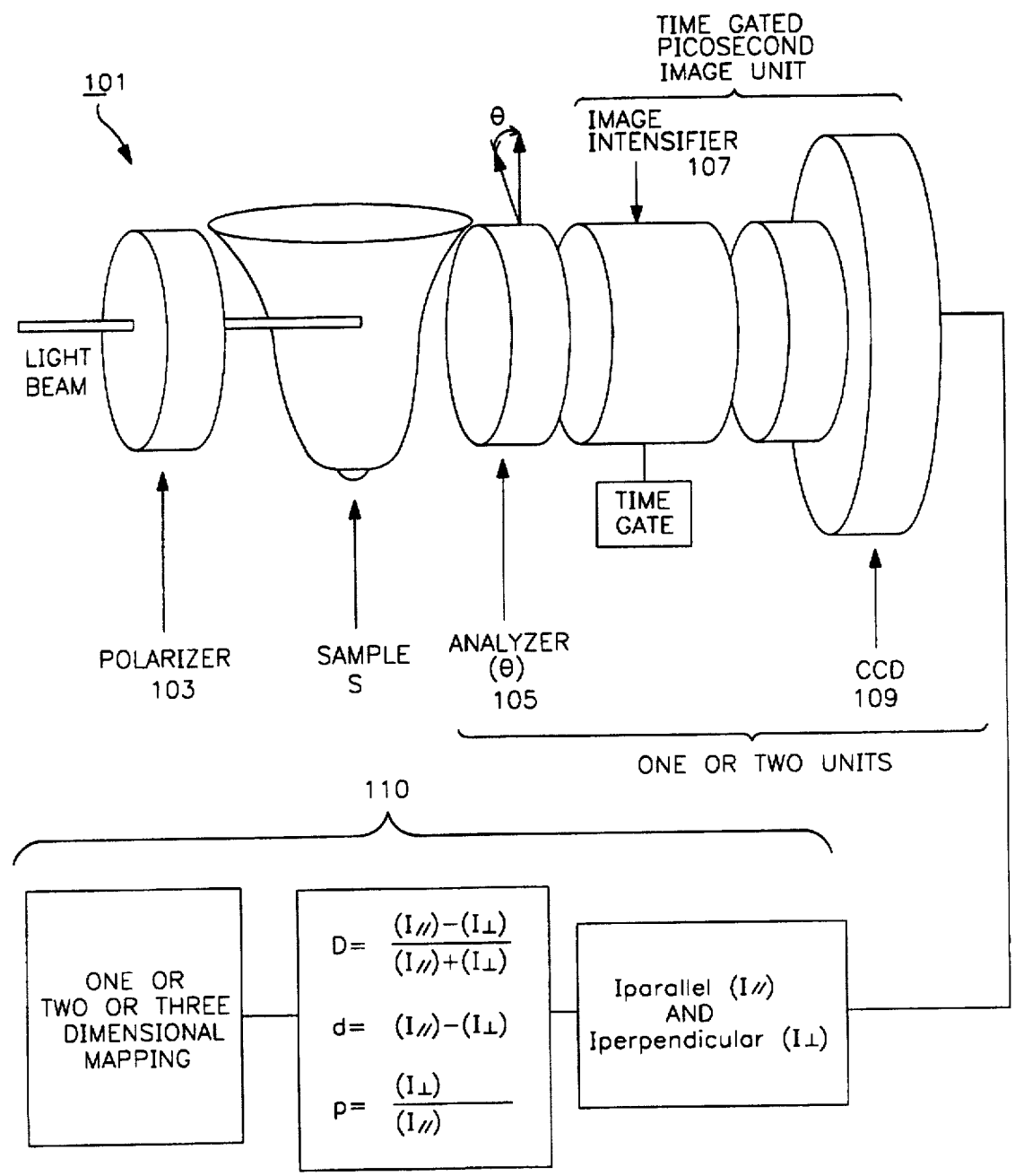
Figure 10:
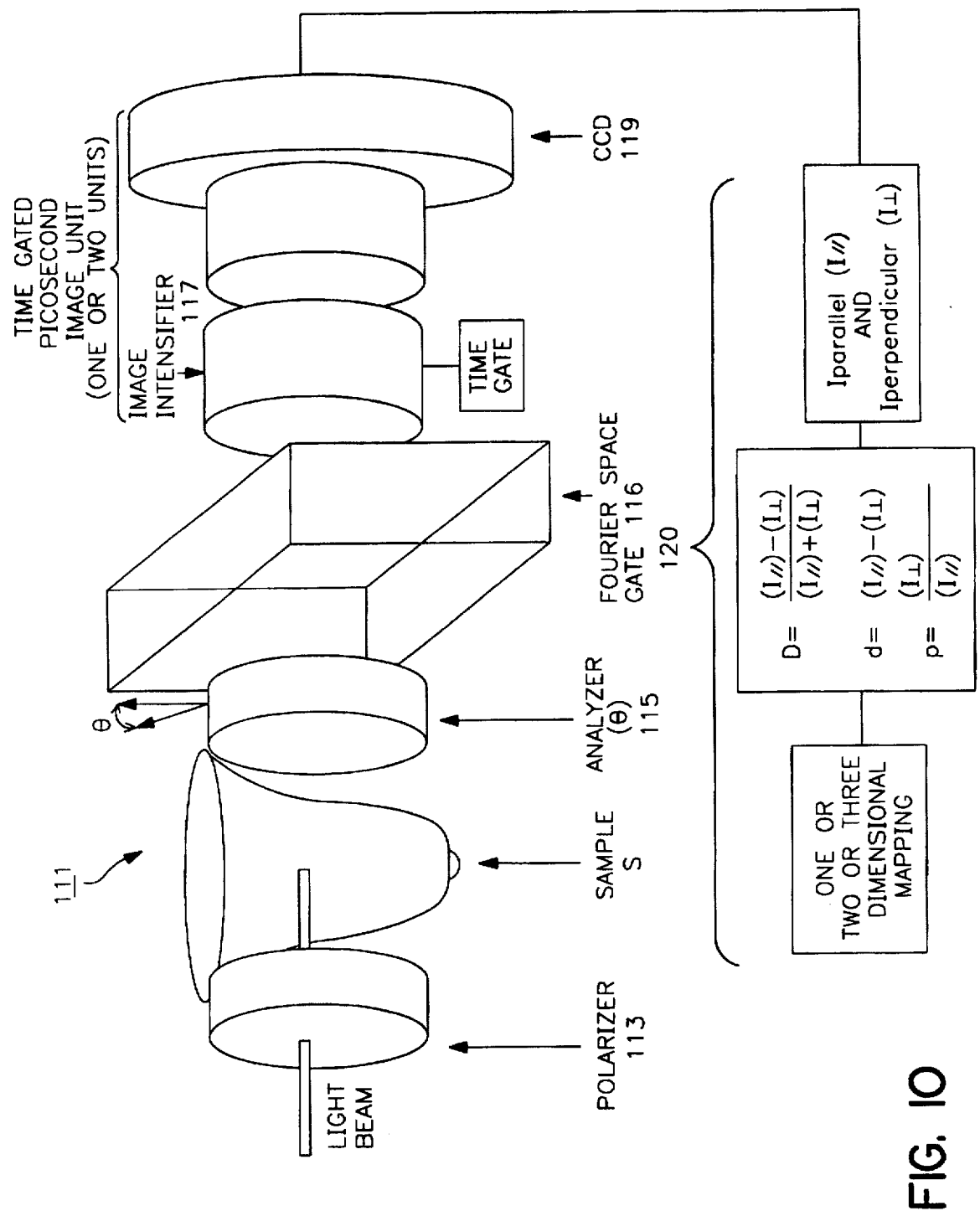
Figure 11:
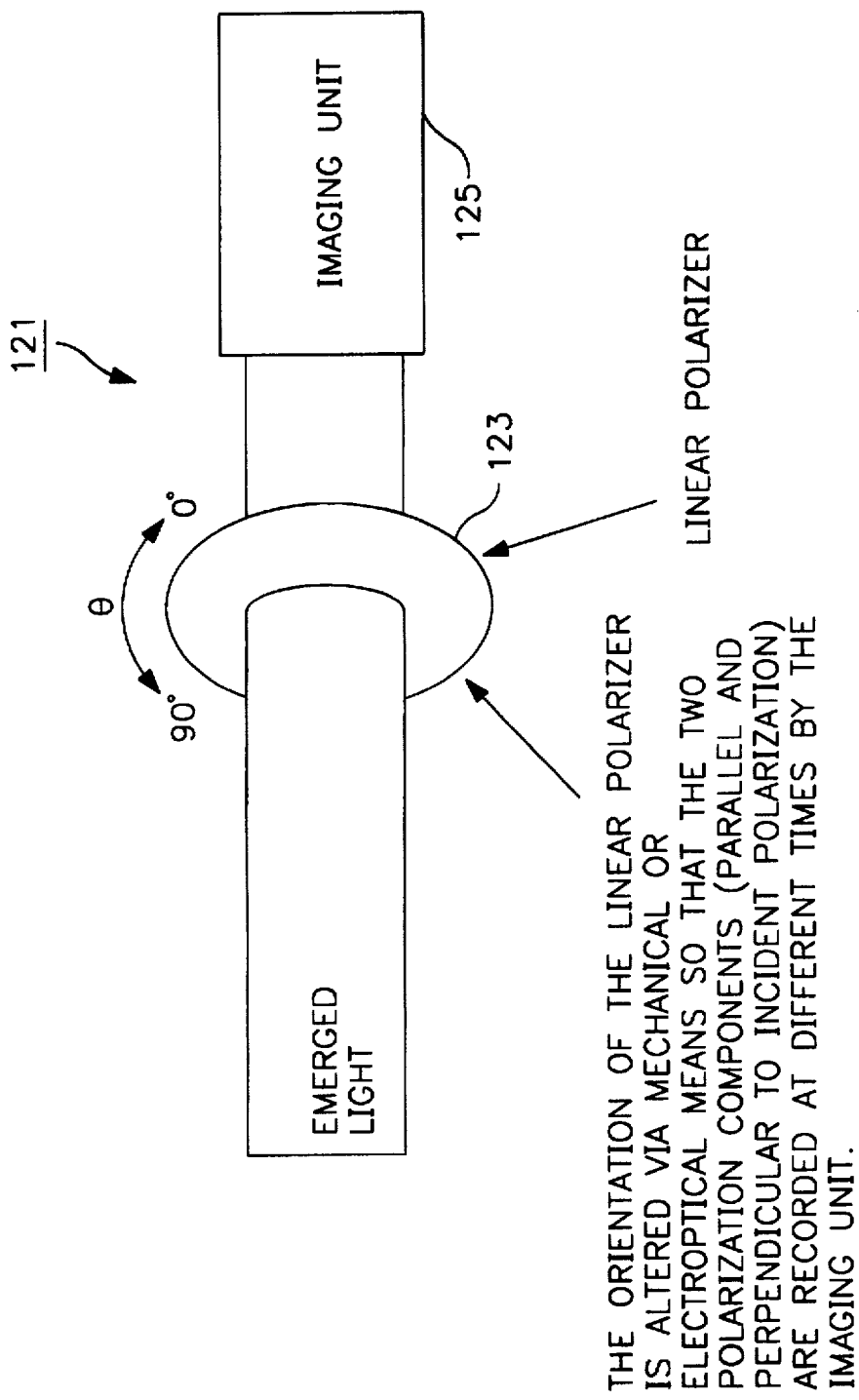
Figure 12:
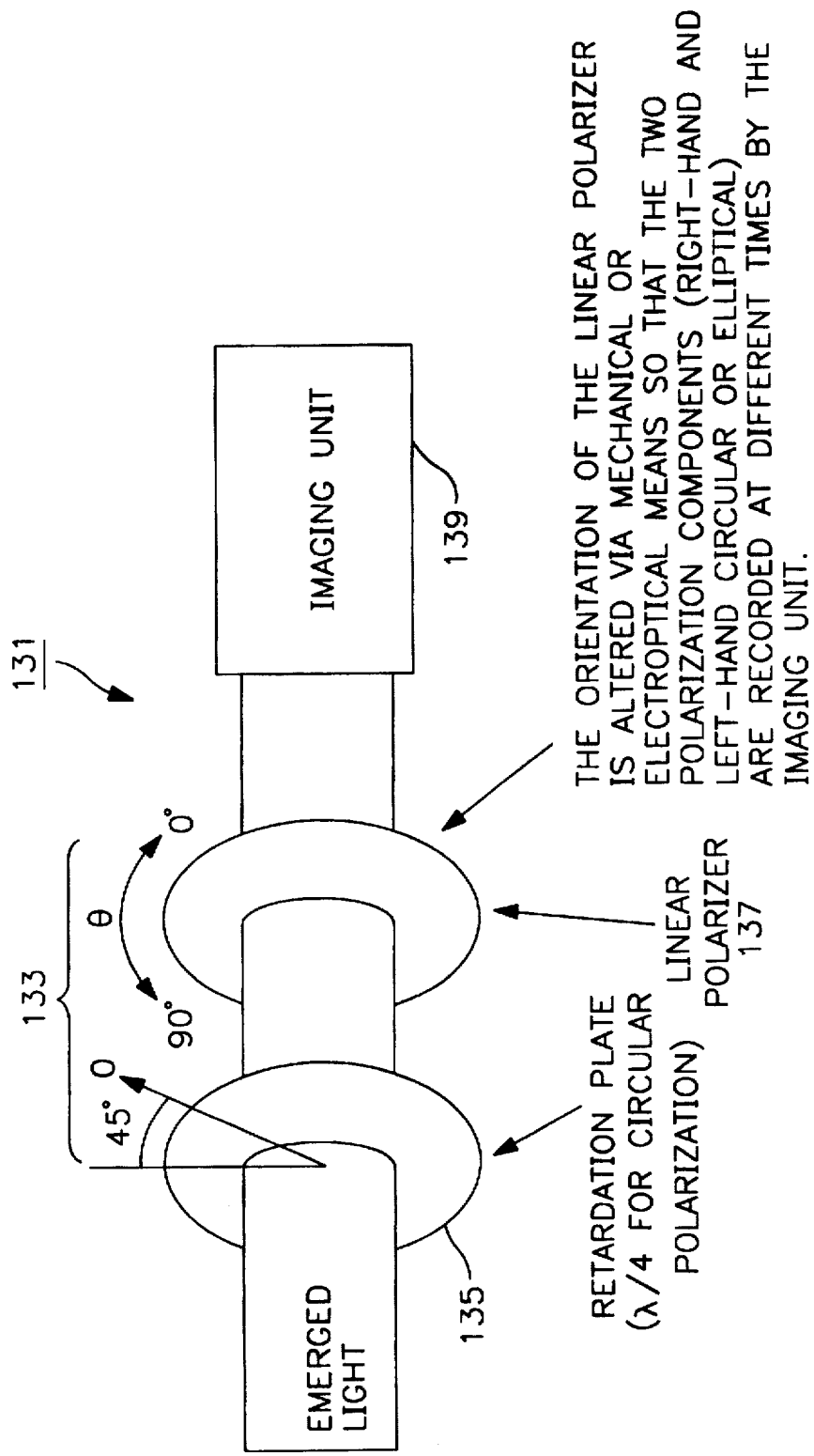
Figure 13:
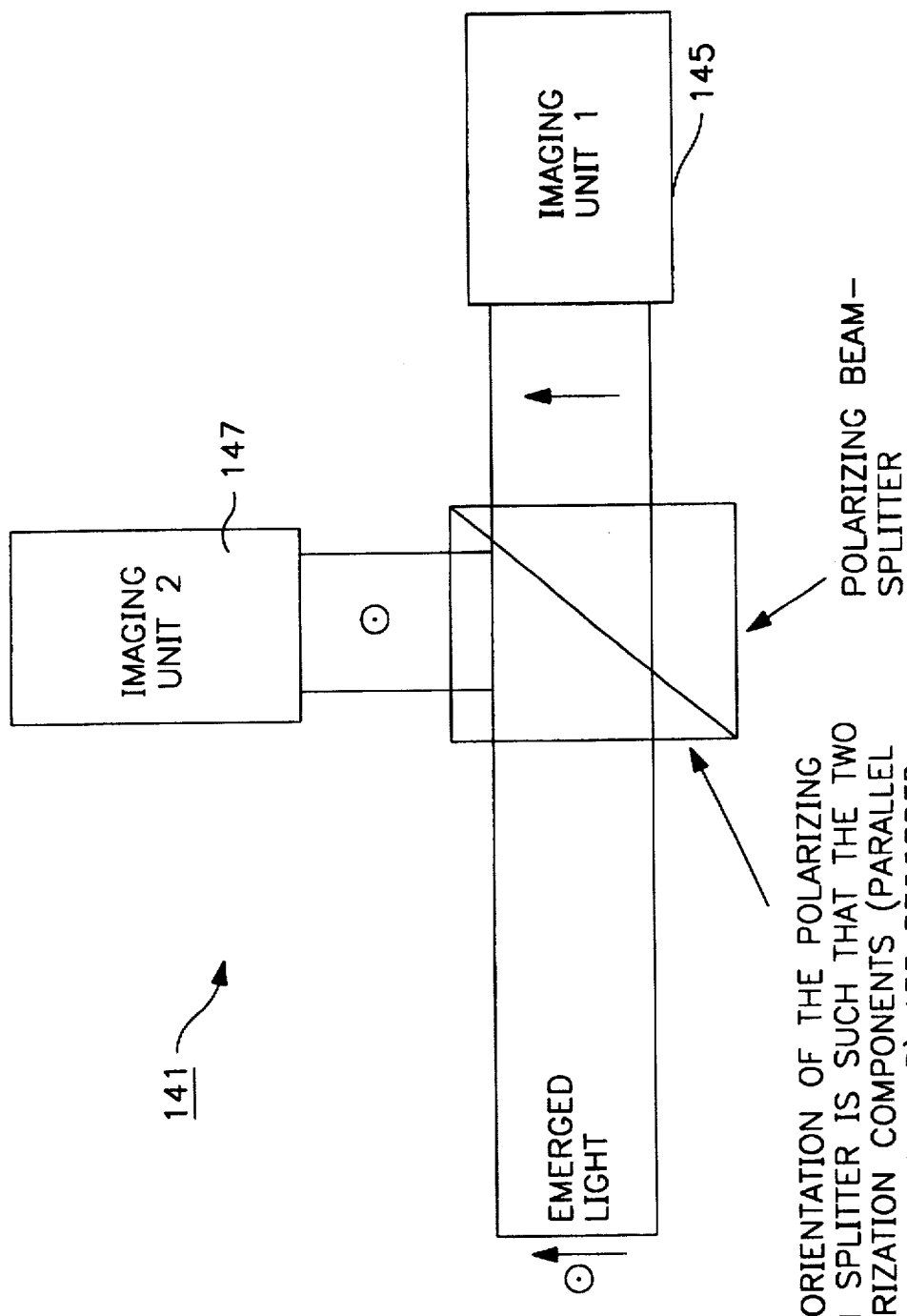
Figure 14:
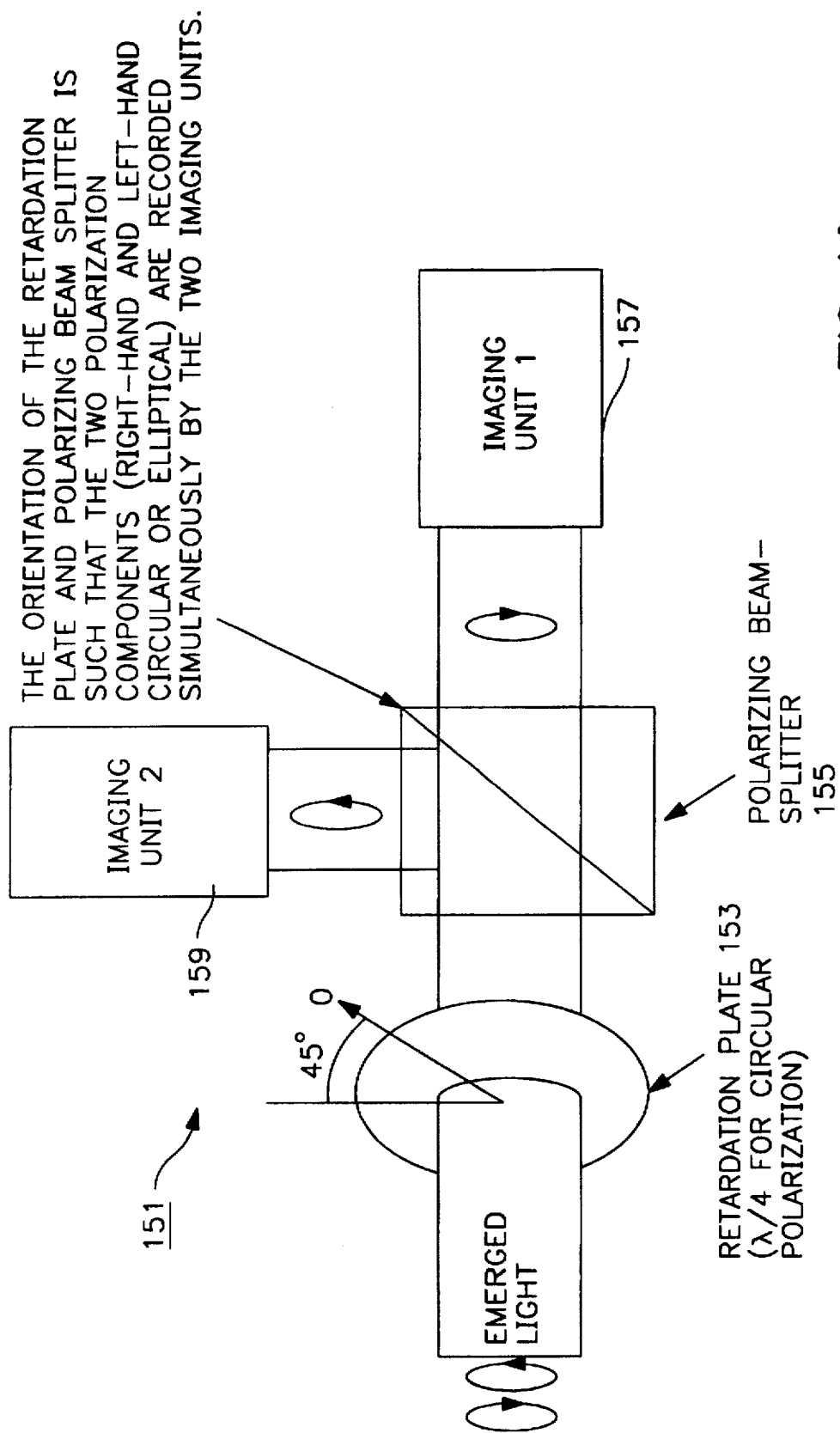
Figure 15:
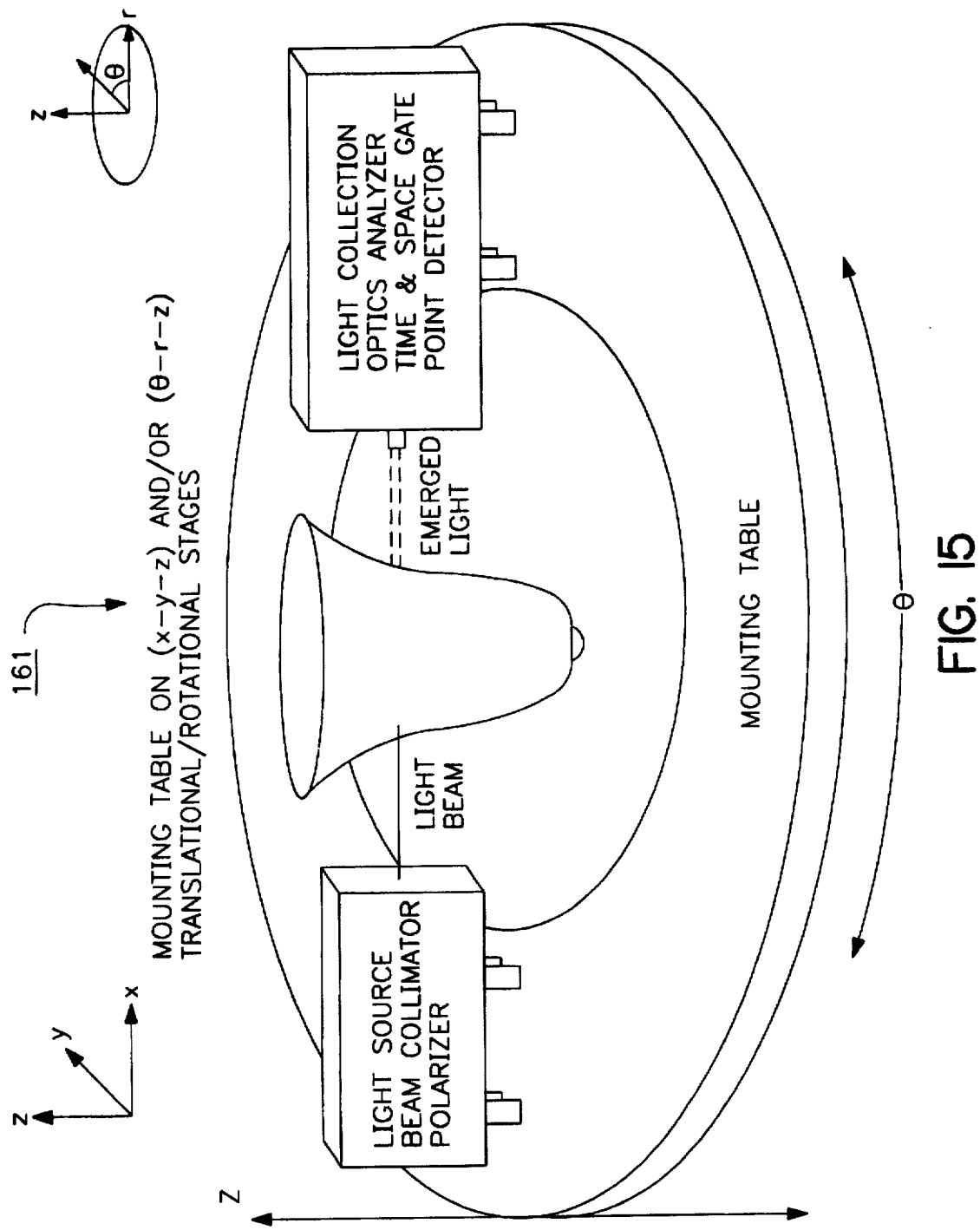
Figure 16A:
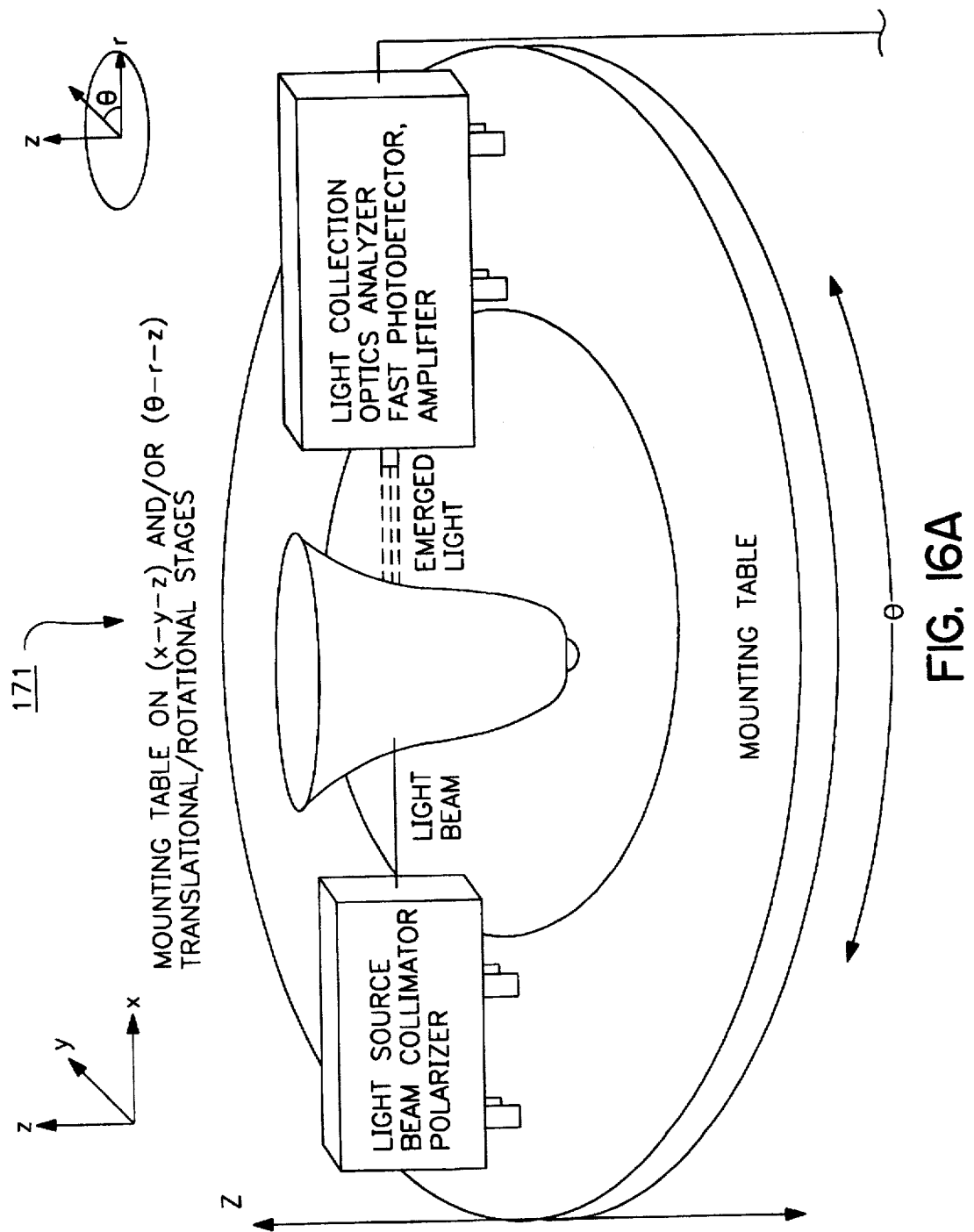
Figure 16B:
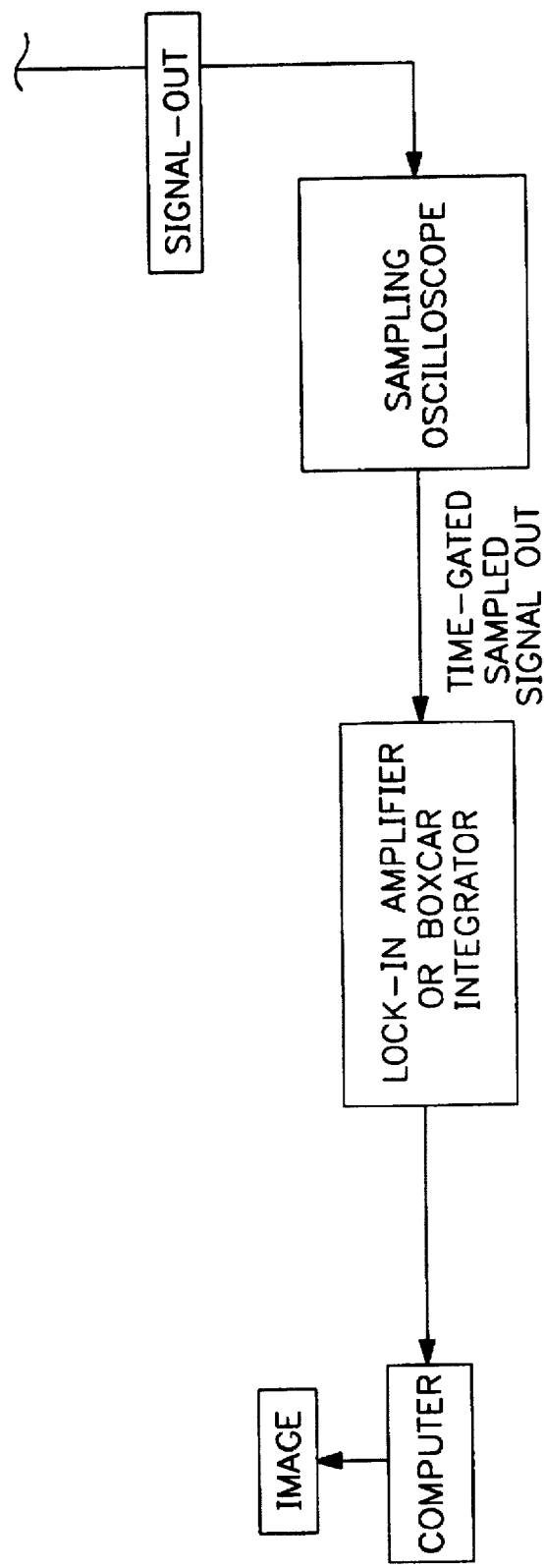
Figure 17:
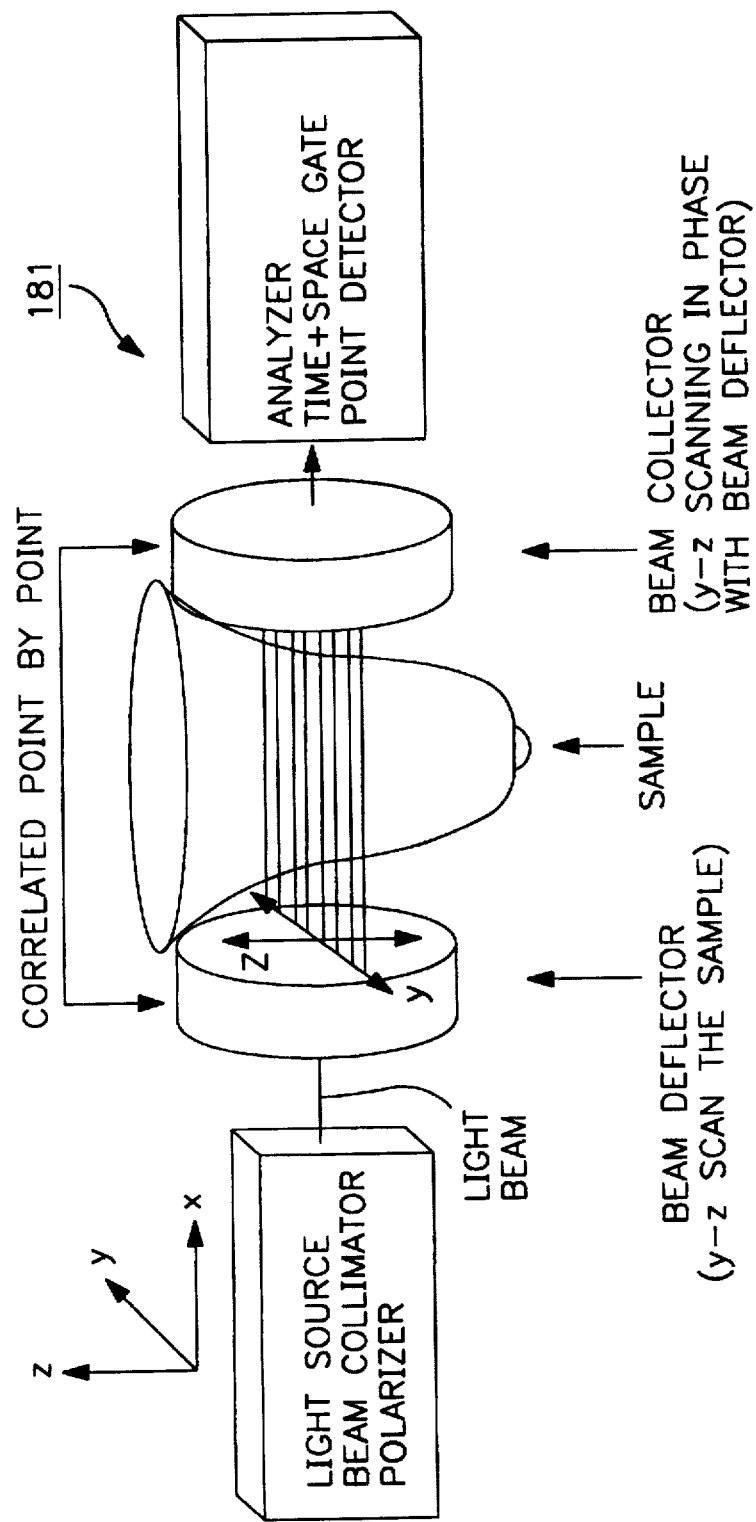
Figure 18:
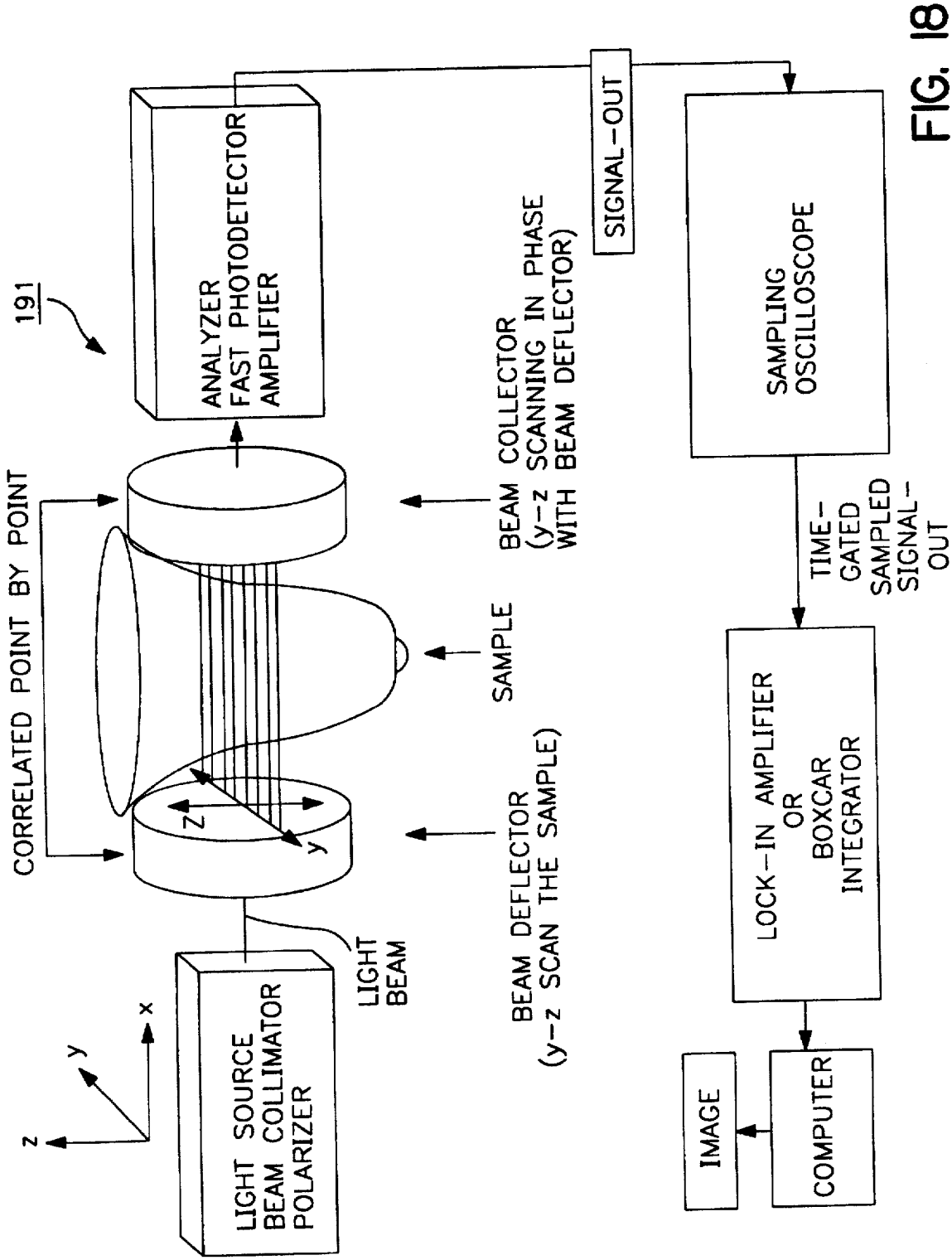
Figure 19:
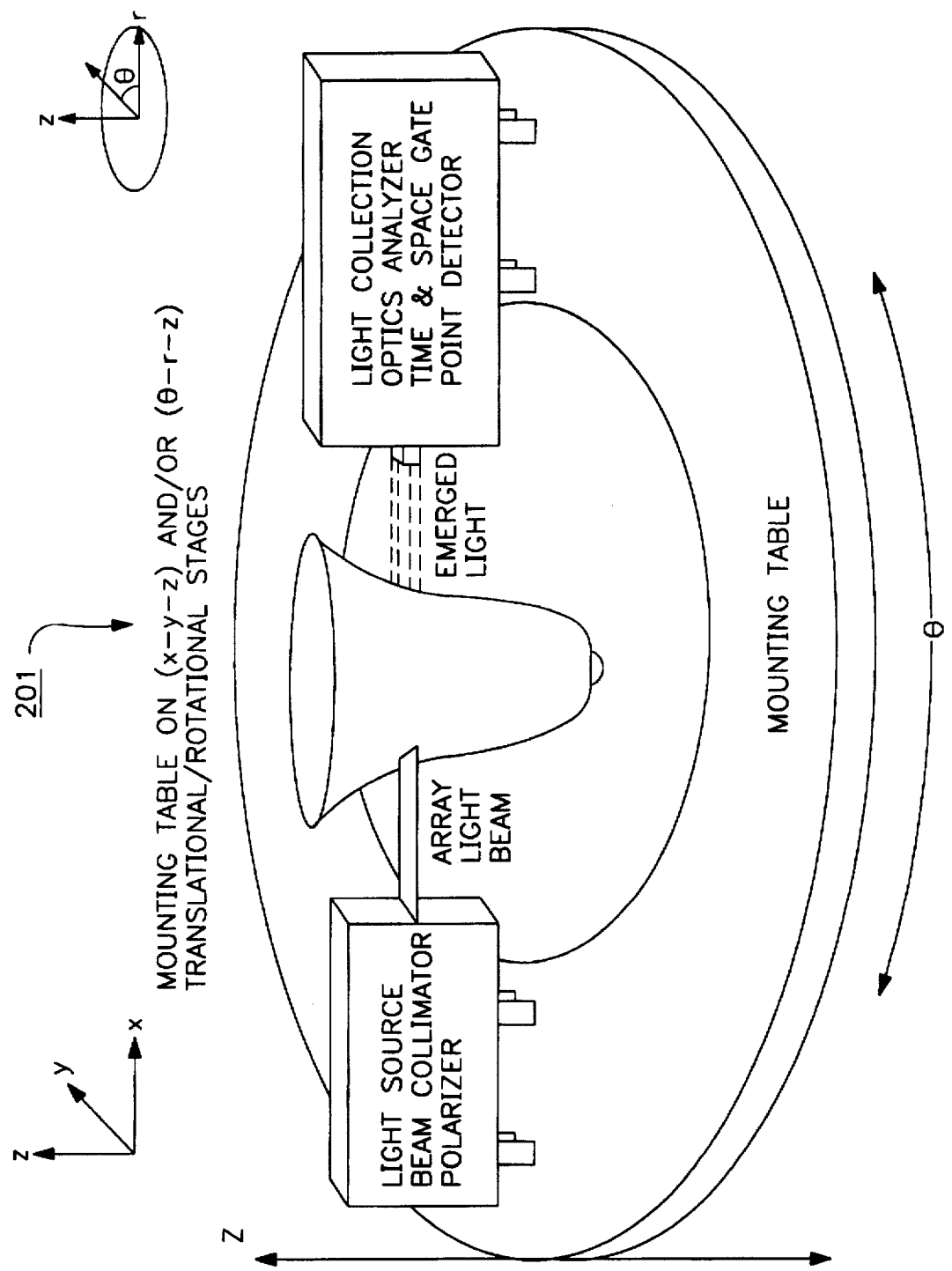
Figure 20:
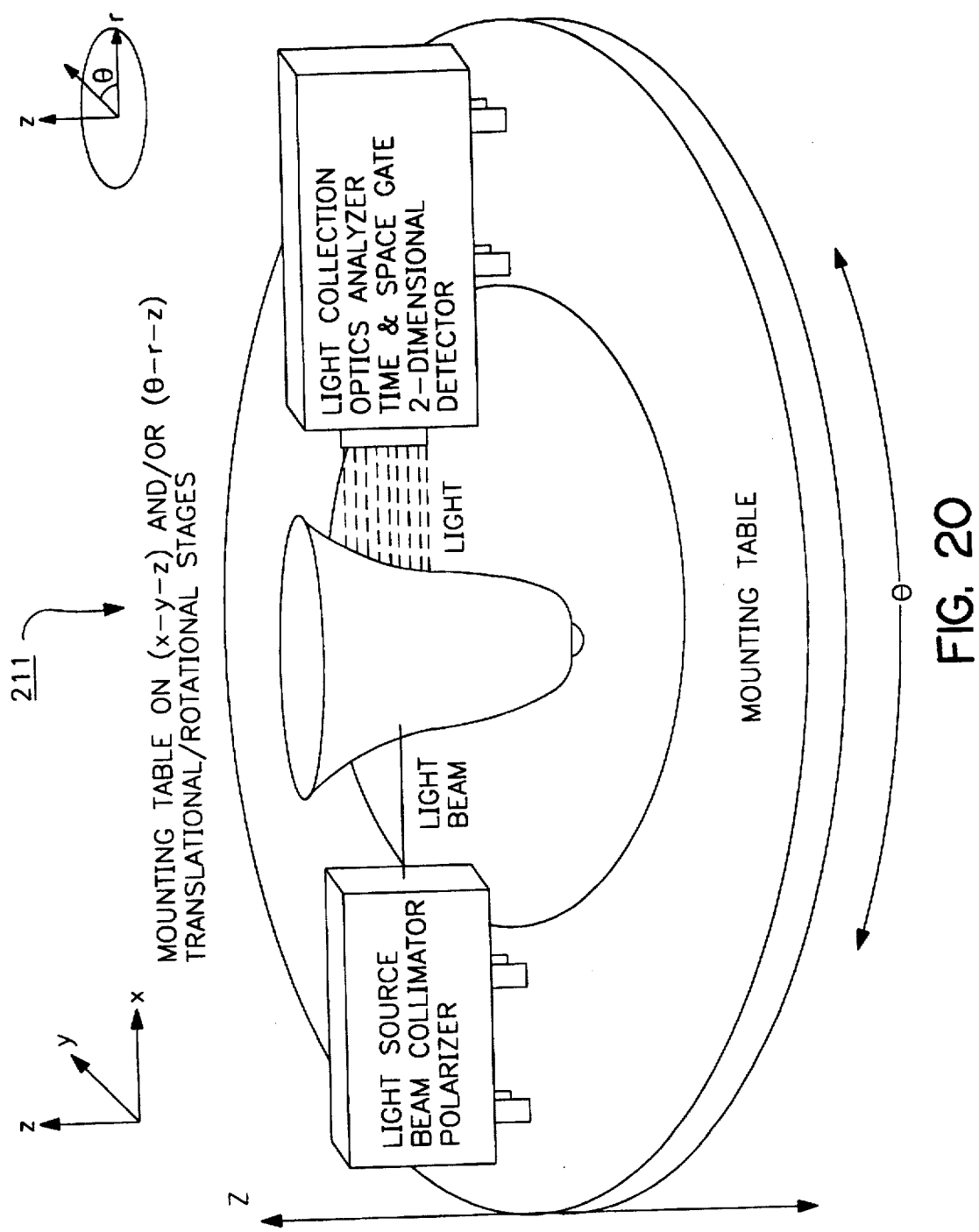
Figure 21:
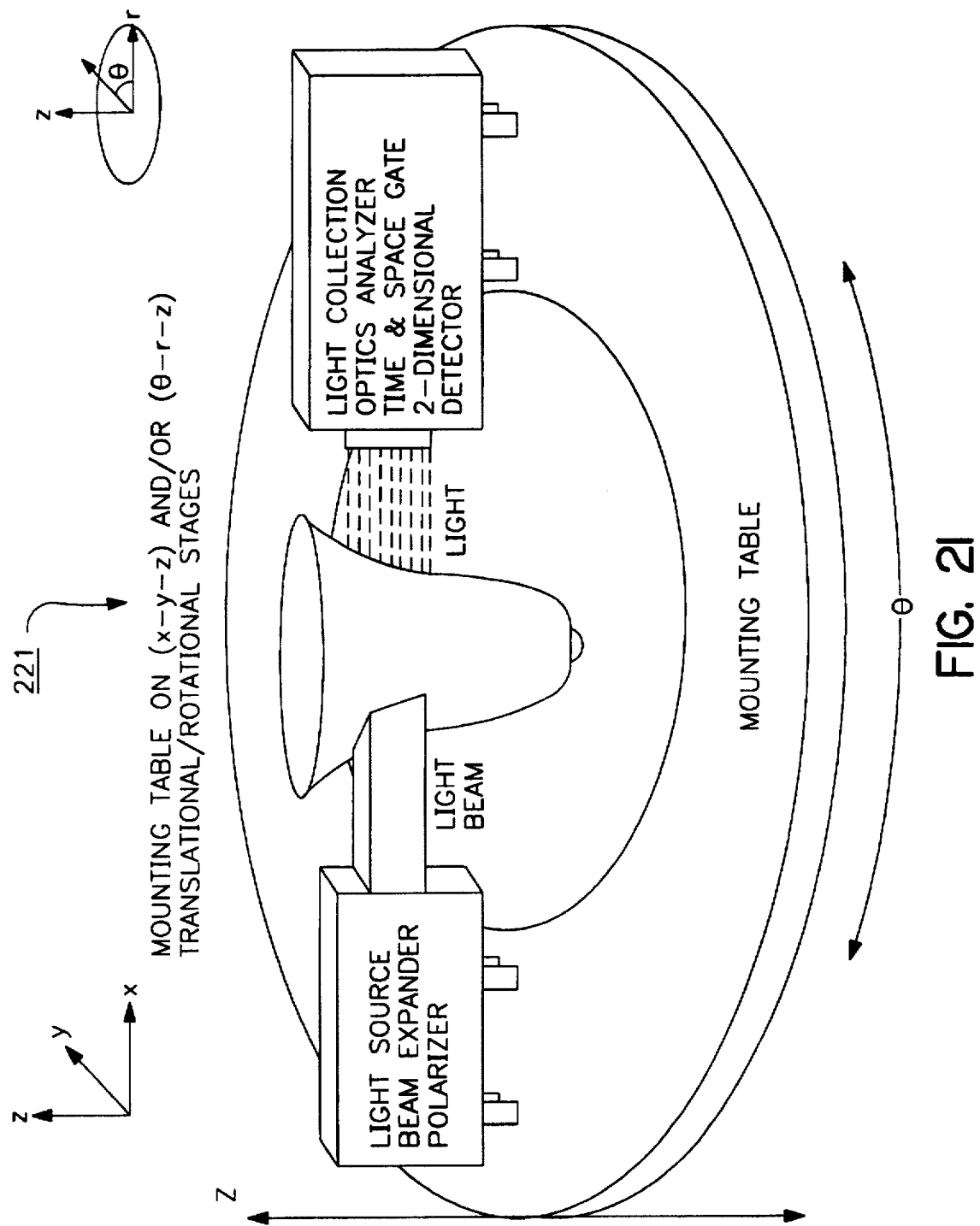
Figure 22A:
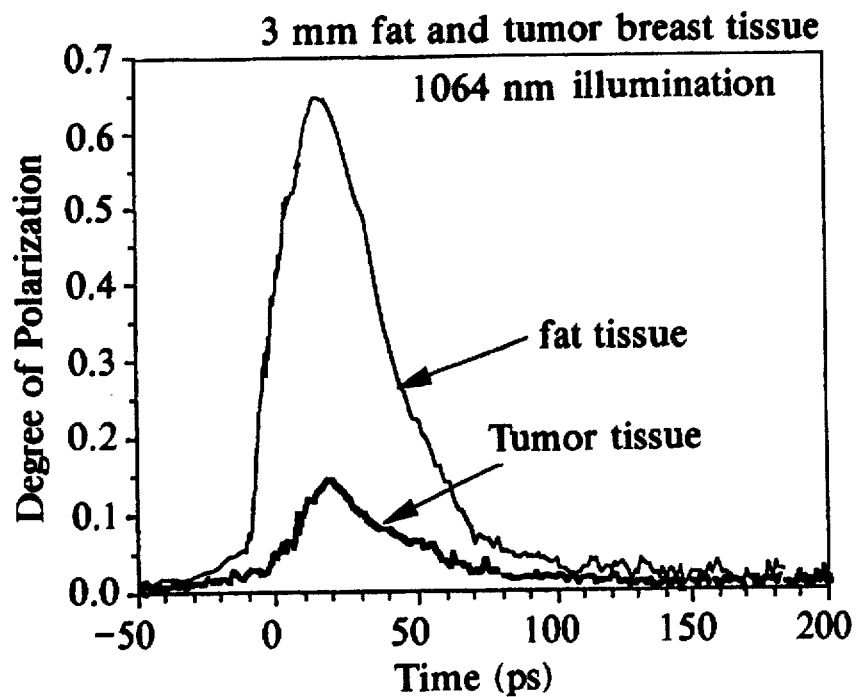
Figure 22B:
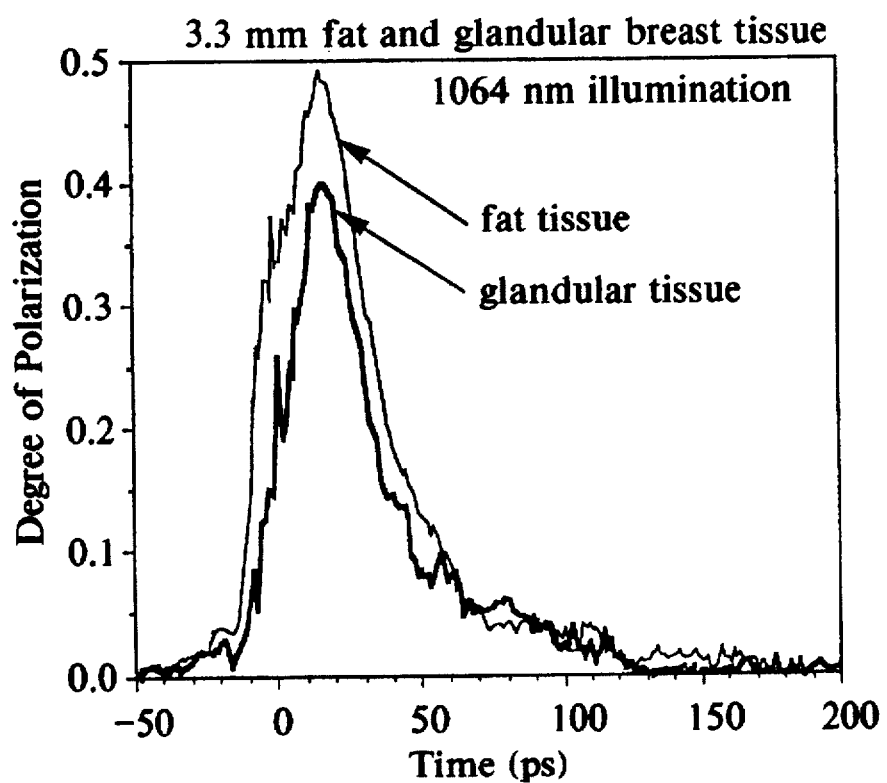
Figure 23:
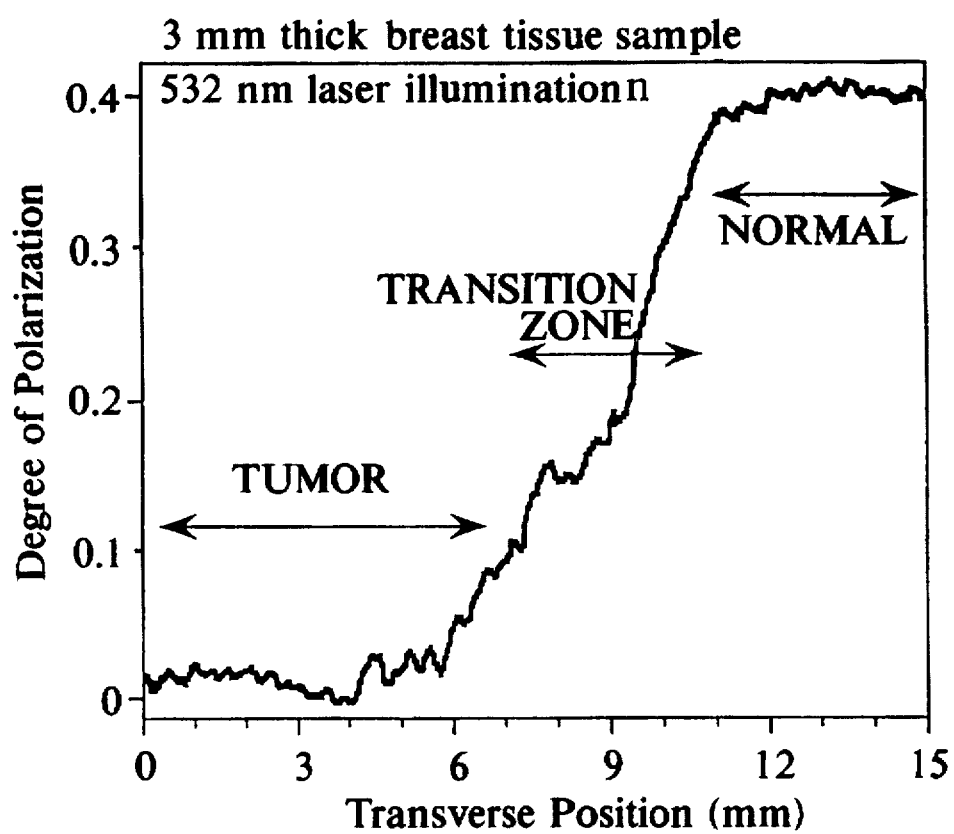

FIG. 6 is a schematic view of a second embodiment of an apparatus for imaging and/or characterizing a tissue, the apparatus being constructed according to the teachings of the present invention;

FIG. 7 is a schematic view of a third embodiment of an apparatus for imaging and/or characterizing a tissue, the apparatus being constructed according to the teachings of the present invention;

FIG. 8 is a schematic view of a fourth embodiment of an apparatus for imaging and/or characterizing a tissue, the apparatus being constructed according to the teachings of the present invention;

FIG. 9 is a schematic view of a fifth embodiment of an apparatus for imaging and/or characterizing a tissue, the apparatus being constructed according to the teachings of the present invention;

FIG. 10 is a schematic view of a sixth embodiment of an apparatus for imaging and/or characterizing a tissue, the apparatus being constructed according to the teachings of the present invention;

FIG. 11 is a schematic view of one type of combination analyzer and imaging system adapted for use in the systems of FIGS. 1 and 6 through 10;

FIG. 12 is a schematic view of a first alternative combination analyzer and imaging system to that shown in FIG. 11;

FIG. 13 is a schematic view of a second alternative combination analyzer and imaging system to that shown in FIG. 11;

FIG. 14 is a schematic view of a third alternative combination analyzer and imaging system to that shown in FIG. 11;

FIG. 15 is a schematic view of a seventh embodiment of an apparatus for imaging and/or characterizing a tissue, the apparatus being constructed according to the teachings of the present invention;

FIG. 16 is a schematic view of an eighth embodiment of an apparatus for imaging and/or characterizing a tissue, the apparatus being constructed according to the teachings of the present invention;

FIG. 17 is a schematic view of a ninth embodiment of an apparatus for imaging and/or characterizing a tissue, the apparatus being constructed according to the teachings of the present invention;

FIG. 18 is a schematic view of a tenth embodiment of an apparatus for imaging and/or characterizing a tissue, the apparatus being constructed according to the teachings of the present invention;

FIG. 19 is a schematic view of an eleventh embodiment of an apparatus for imaging and/or characterizing a tissue, the apparatus being constructed according to the teachings of the present invention;

FIG. 20 is a schematic view of a twelfth embodiment of an apparatus for imaging and/or characterizing a tissue, the apparatus being constructed according to the teachings of the present invention;

FIG. 21 is a schematic view of a thirteenth embodiment of an apparatus for imaging and/or characterizing a tissue, the apparatus being constructed according to the teachings of the present invention;

FIGS. 22(a) and 22(b) are graphic representations of the temporal profiles of the degree of polarization of the emergent light under 1064 nm laser pulsed illumination of human breast tissue for (a) 3 mm fat and cancer tissue samples obtained from a patient; and (b) 3.3 mm fat and glandular tissue samples obtained from the same patient, respectively; and FIG. 23 is a graphic representation of the degree of polarization in the transverse position of 532 nm laser light transmitted through 3 mm thick breast tissue sample containing a cancerous tumor section.

DETAILED DESCRIPTION OF PREFERRED EMBODIMENTS

The present invention is based, in part, on the discovery that, when initially polarized light is transmitted through a turbid medium, such as human tissue, the ballistic and snake-like components of the light emergent from the turbid medium maintain the polarization of the initially polarized light while the diffuse component of the light emergent from the turbid medium becomes completely depolarized. The present invention is also based, in part, on the discovery that initially polarized light transmitted through a turbid medium, such as human tissue, maintains its polarization, to a lesser or greater extent, depending upon the wavelength of the initially polarized light and depending upon the type of turbid medium traversed.

In accordance with the present invention, the foregoing discoveries can be used to, among other things, improve the optical imaging quality of optical tomography and mammography applications, by doing the following: a) improving the time-gating of the ballistic and snake light components of light emergent from a tissue when polarized laser pulses are used to image the tissue; b) selectively collecting forwardly propagating light in the case of continuous or pulsed light input; and c) enabling the characterization of the type of human tissue tested based on the degree that the tissue preserves polarization at different wavelengths.

Human breast tissue comprises fat tissue, glandular tissue, cysts and tumor tissue (both benign and malignant). For optical mammography, one needs to be able to image and to distinguish the various types of tissues; moreover, it would be highly desirable to be able to distinguish between benign and malignant tumor tissues.

Figure 1:
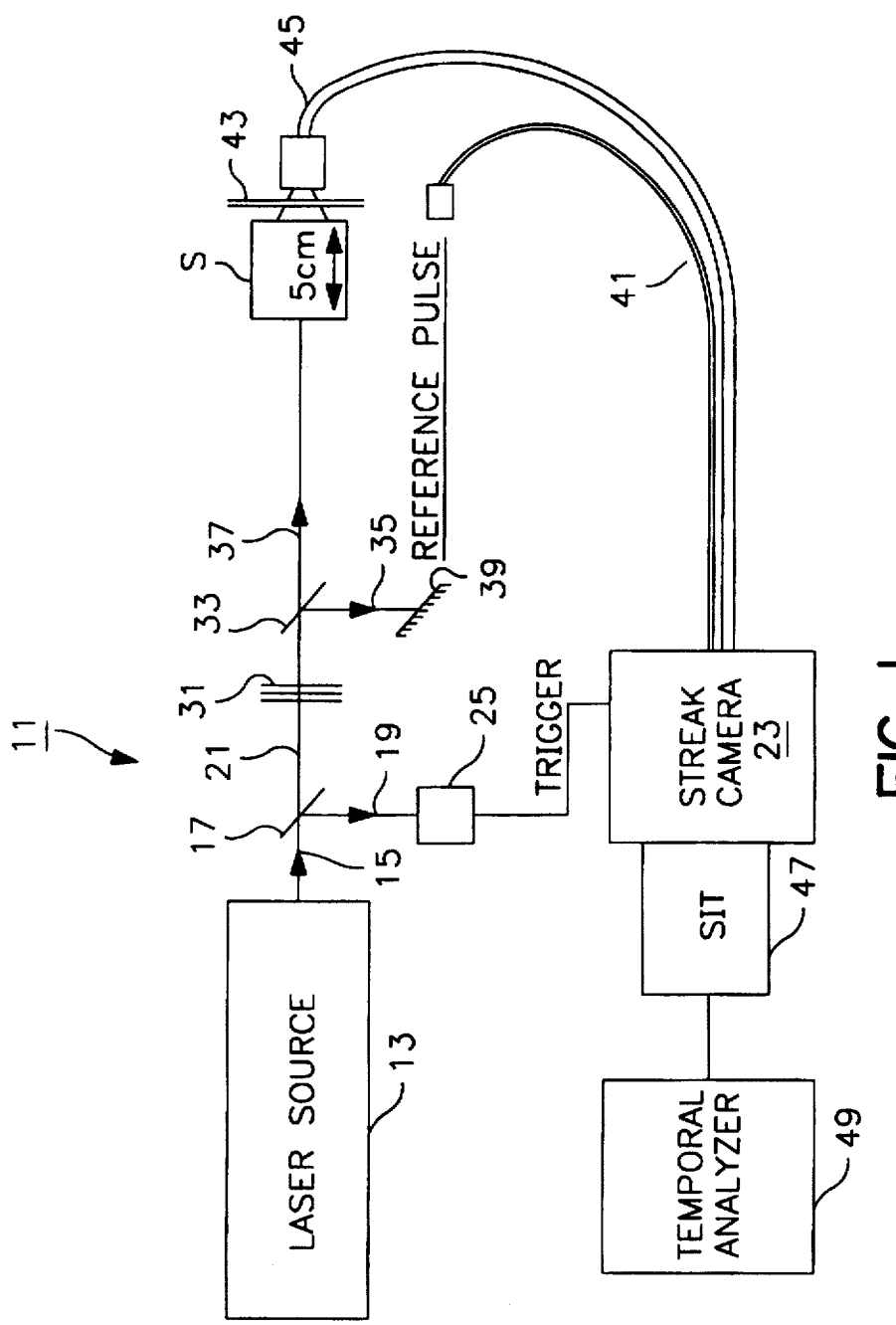
FIG. 1 is a schematic view of a first embodiment of an apparatus for imaging and/or characterizing a tissue, the apparatus being constructed according to the teachings of the present invention.

Referring now to FIG. 1, there is schematically shown an experimental set-up of an apparatus constructed according to the teachings of the present invention for imaging and/or characterizing a tissue, the apparatus being represented generally by reference numeral 11.

Apparatus 11 comprises a laser source 13. In the present embodiment, laser source 13 comprises a mode-locked Nd:YAG laser for producing a series of laser pulses 15. Laser pulses 15 are 6.5 ps pulses at 1064 nm with a repetition rate of 82 MHz and/or, at a second harmonic thereof, 5 ps pulses at 532 nm. Apparatus 11 also includes a beam splitter 17 for splitting each pulse 15 into a pair of pulses 19 and 21. Pulse 19 is used to trigger a streak camera 23. A photodiode 25 is disposed along the path of pulse 19 before streak camera 23 so that pulse 19 triggers streak camera 23 at an appropriate time.

Apparatus 11 also includes a first polarizer 31 disposed along the path of pulse 21, polarizer 31 being oriented parallel to the initial state of polarization of pulse 21 to ensure the polarization thereof. A beam splitter 33 is disposed after first polarizer 31 for splitting pulse 21 into a pair of pulses 35 and 37. Pulse 35, which is used as a reference pulse, is deflected off a mirror 39 and is transmitted to streak camera 23 by a collection optical fiber 41 having a diameter of 110 μm. Pulse 37, which has an average power of about 400 mW and a diameter of 3 mm, is used for propagation through a tissue sample, which may be, for example, breast tissue samples having a thickness of about 3 mm or 12 mm in a holder having a thickness of about 5 cm.

Apparatus further includes a polarizer 43 disposed on the opposite side of the sample upon which pulse 37 is incident. For reasons to become apparent below, polarizer 43 may be oriented either parallel to the initial state of polarization of polarizer 31 or perpendicular to the initial state of polarization of polarizer 31 for use as an analyzer of the polarization state of the emergent light. Apparatus also includes a fiber bundle 45, which is used for the collection of light passed through polarizer 43 and for the transmission of said light to streak camera 23. Bundle 45 is approximately 1.2 mm in diameter and comprises a plurality of fibers of 110 mm in diameter. The end of bundle 45 coupled to the input of streak camera 23 has its fiber elements aligned in a line 7.5 mm in length and 110 mm thickness. Fiber 41 is coupled to bundle 45 2 mm on the side of the 7.5 mm line of bundle 45. Streak camera 23, which produces temporal profiles of the light signals inputted thereinto through fiber 41 (reference signal) and bundle 45 (propagation signal), has its output coupled to a silicon-intensified-target (SIT) 47. Streak camera 23/SIT 47 has a temporal resolution capability of about 10 ps.

Apparatus 11 further includes a temporal analyzer 49 which receives the output from streak camera 23/SIT 47.

Figure 2A:
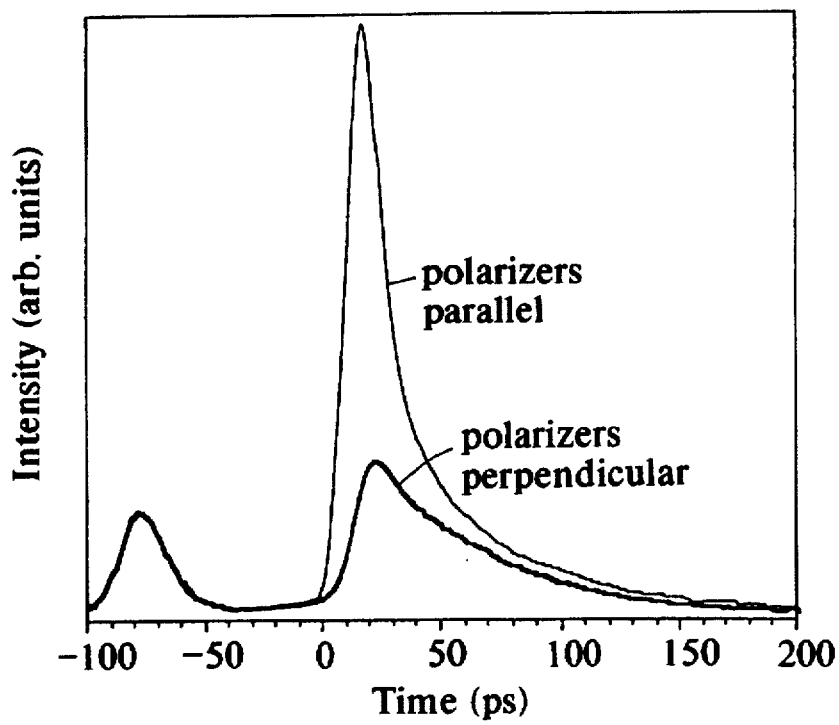
FIGS. 2(a) and 2(b) are graphic representations of light intensity measured as a function of time using the apparatus of FIG. 1 for a human breast fat tissue sample and a human breast tumor tissue sample, respectively, the apparatus of FIG. 1 being arranged so as to illuminate the samples with 6.5 ps pulses of polarized light having a wavelength of 1064 nm, the thin line representing light intensity measured with the pair of polarizers of the apparatus of FIG. 1 oriented parallel to one another, the thick line representing light intensity measured with the pair of polarizers oriented perpendicular to one another.
Figure 2B:
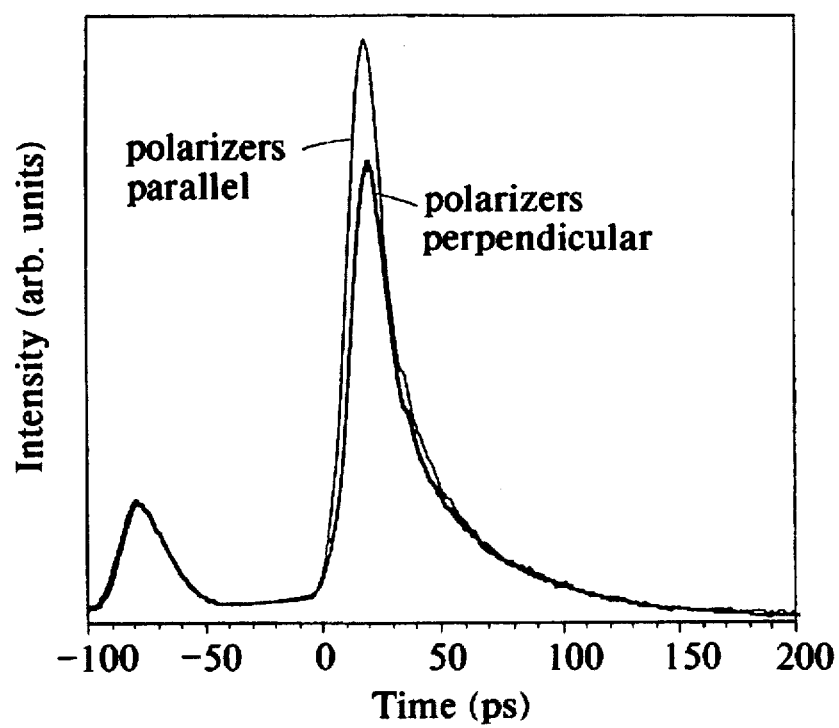

FIGS. 2(a) and 2(b) show the intensity of the output pulses emergent from a fat tissue sample 3 mm in thickness and from a malignant tumor tissue sample 3 mm in thickness, respectively, with polarizers 31 and 43 parallel to one another (thin line) and perpendicular to one another (thick line) when laser pulses 6.5 ps in duration with a wavelength of 1064 nm were illuminated therewith. In FIGS. 2(a) and 2(b), zero time is the time that the incident pulse enters the sample while the first pulse at negative time (−80 ps) is the reference pulse.

Figure 3A:
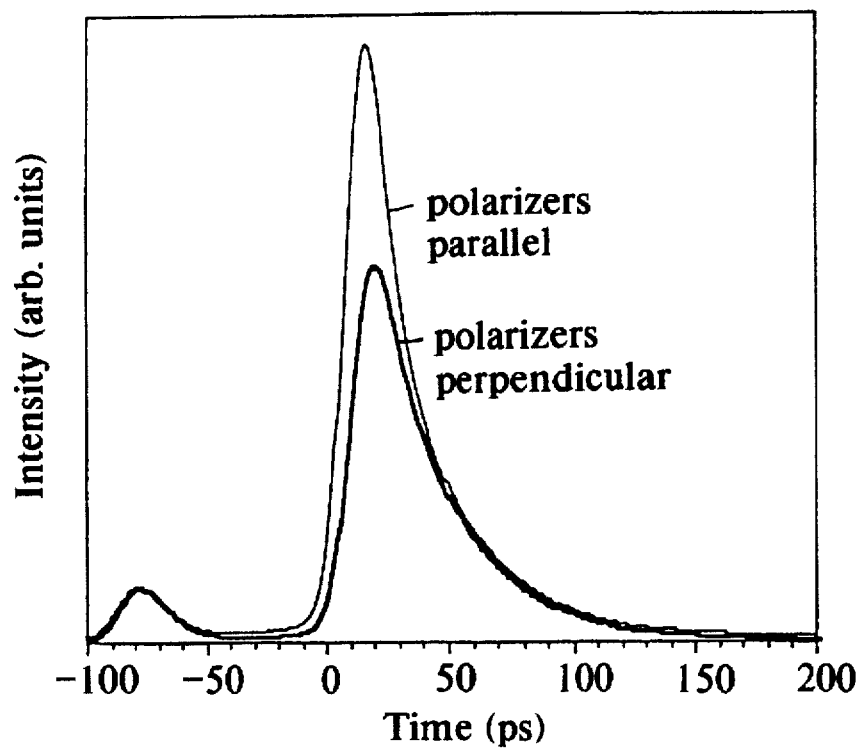
FIGS. 3(a) and 3(b) are graphic representations of light intensity measured as a function of time using the apparatus of FIG. 1 for a human breast fat tissue sample and a human breast tumor tissue sample, respectively, the apparatus of FIG. 1 being arranged so as to illuminate the samples with 5 ps pulses of polarized light having a wavelength of 532 nm, the thin line representing light intensity measured with the pair of polarizers of the apparatus of FIG. 1 oriented parallel to one another, the thick line representing light intensity measured with the pair of polarizers oriented perpendicular to one another.
Figure 3B:
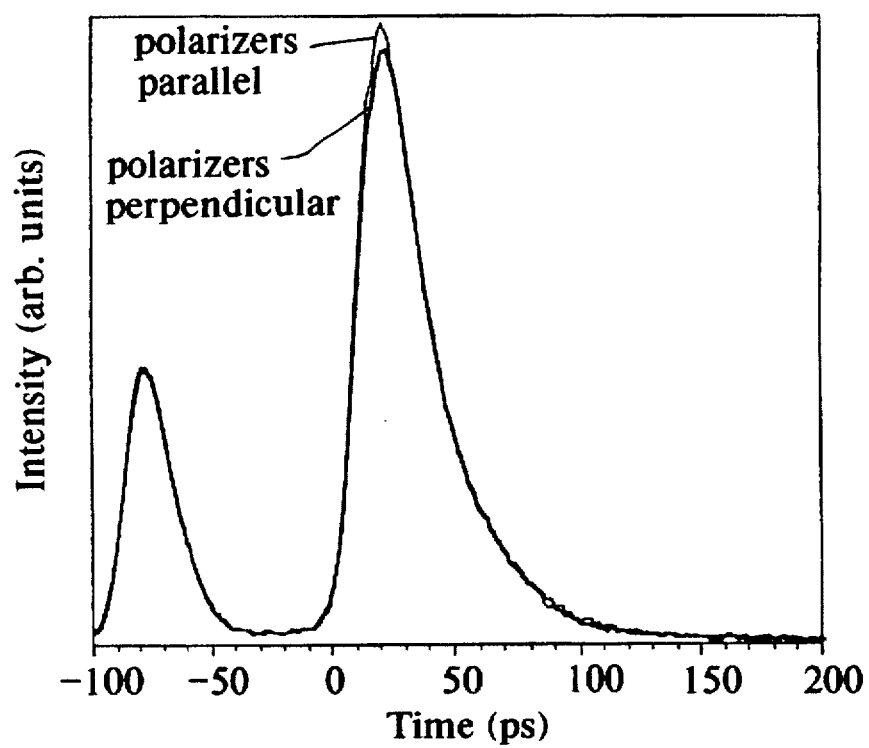

FIGS. 3(a) and 3(b) show the same types of intensity profiles obtained from the same samples as in FIGS. 2(a) and 2(b), the only difference being that the incident laser pulses in FIGS. 3(a) and 3(b) are 5 ps in duration with a wavelength of 532 nm.

Figure 4:
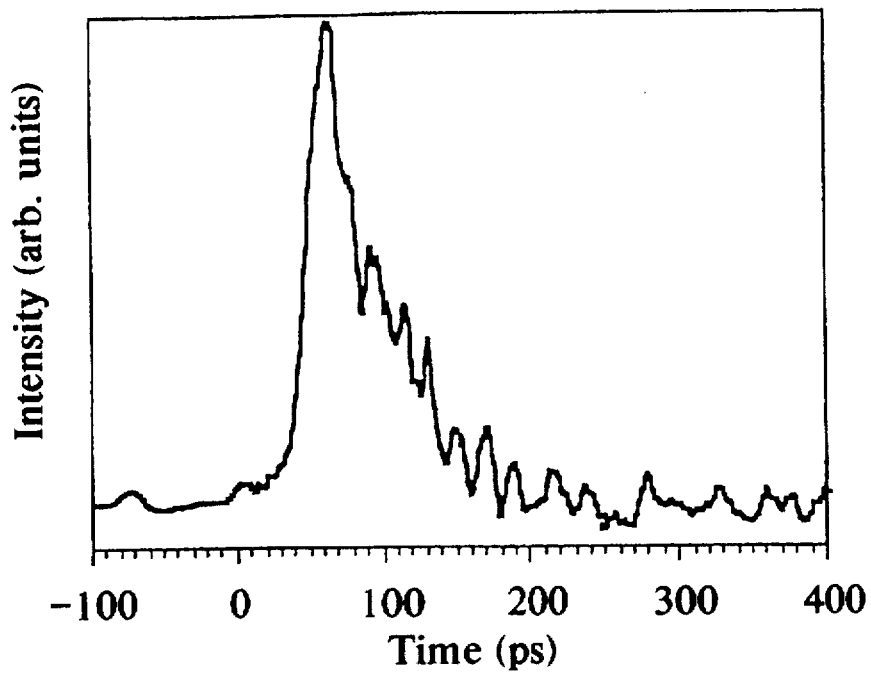
FIG. 4 is a graphic representation of the temporal light intensity profile obtained for a human breast malignant tumor tissue by subtracting the light intensity measured as a function of time using the apparatus of FIG. 1 with the pair of polarizers oriented perpendicular to one another from the light intensity measured as a function of time using the apparatus of FIG. 1 with the pair of polarizers oriented parallel to one another.

FIG. 4 shows the temporal profile resulting from the subtraction of the components of the output pulse parallel and perpendicular to the incident polarization when 1064 nm laser pulses were used to propagate through 12 mm thick cancer breast tissue. The intensity difference profile extends only 100 ps after the arrival of the ballistic component while the output pulse extends for over 500 ps. This means that by subtracting the parallel and perpendicular components of the output pulse we can selectively measure the signal from the early part of the output profile. This technique can be used as a time gate to select the early portion of the output pulse to improve imaging of objects in scattering media.

The spectral and temporal degree of polarization $D(\lambda,t)$ of the output pulse is given by the following equation:

$$D(\lambda, t) = \frac{I(\lambda, t)_{parallel} - I(\lambda, t)_{perpendicular}}{I(\lambda, t)_{parallel} + I(\lambda, t)_{perpendicular}} \quad (1)$$

where $I(\lambda,t)_{parallel}$ and $I(\lambda,t)_{perpendicular}$ are the components of the output pulse with polarization parallel and perpendicular to the incident polarization respectively. The peak values of the degree of polarization will be denoted by D. Other useful representations of data for imaging include: $P=(I_{perpendicular})/(I_{parallel})$ and $d=I_{perpendicular}-I_{parallel}$.

Figure 5:
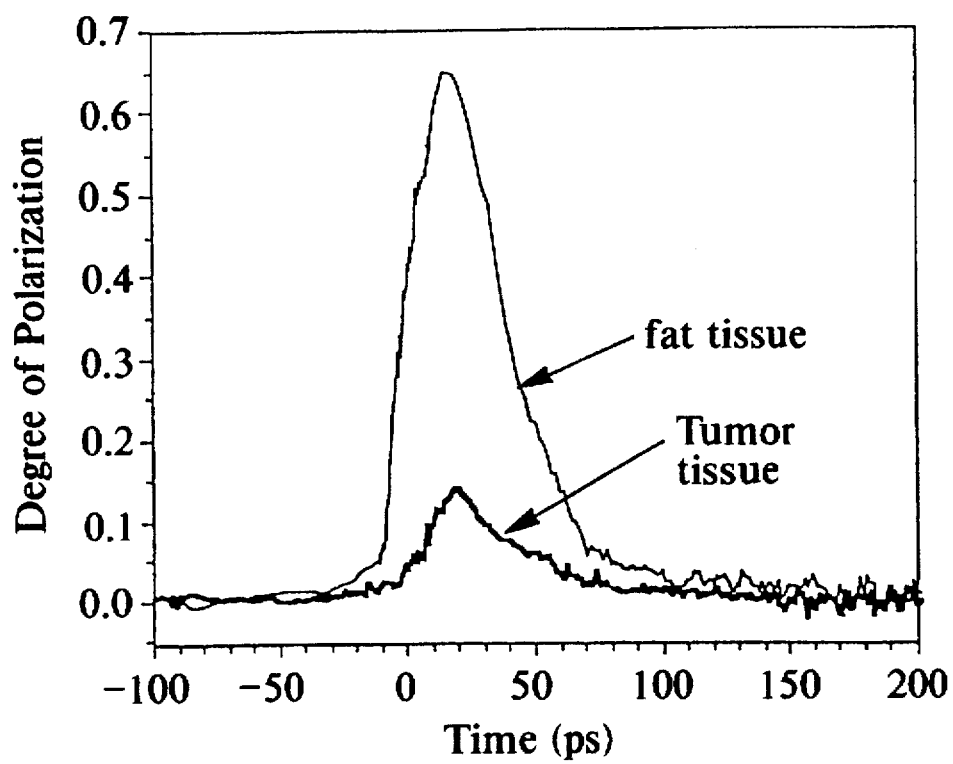
FIG. 5 is a graphic representation of the degree of polarization $D(\lambda,t)$ intensity measurements of FIGS. 2(a) and 2(b) for a human breast fat tissue sample and a human breast minor tissue sample, respectively, fitted to the equation.

FIG. 5 displays the temporal profiles of the degree of polarization D(t) using 1064 nm laser pulses to propagate the 3 mm thick fat (thin line) and tumor (thick line) tissues obtained using Eq. 1 and the polarized intensity profiles of the output pulse shown in FIGS. 2(a) and 2(b). The estimated peak value of the degree of polarization of the experimental profiles shown in FIGS. 2(a) and 2(b) under 1064 nm excitation are for fat tissue $D^{1064\ nm}_{fat}=0.652$ and for cancer tumor tissue $D^{1064\ nm}_{tumor}=0.148$. The degree of polarization estimated from the profiles shown in FIGS. 3(a) and 3(b) using 532 nm laser pulses are $D^{532\ nm}_{fat}=0.324$ and $D^{532\ nm}_{tumor}=0.0185$.

Without wishing to be limited by any particular theory of the invention, it is believed that tissues depolarize polarized pulses to different degrees due to changes in their structure and makeup. This effect is demonstrated by the fact that $D_{fat}$ is different than $D_{tumor}$. This suggests that, by measuring the degree of polarization spatially $D(\lambda,t,R)$, where R represents the spatial coordinates of the sample, information can be obtained on the type of tissue under investigation and can be used to image an object located inside the tissue. Combining this observation with the fact that the signal measured $(I_{parallel}-I_{perpendicular})$ contains only the ballistic and snake components of the output pulses, which are the components used for imaging, images can be obtained in tissues containing information about the type and location of the tissues under investigation. The spatial change of the degree of polarization ΔD(R) can be used to image regions of tissues which have different components such as cysts, tumors, fat, etc. The ratio of the degree of polarization during propagation of 1064 and 532 nm laser light in fat and cancer breast tissue samples are different. This is shown in FIGS. 2(a), 2(b), 3(a) and 3(b). More specifically, the peak value D of the degree of polarization for several different components has been determined to be as follows:

$$\frac{D_{fat}^{1064 nm}}{D_{fat}^{532 nm}} = 2.01,$$

$$\frac{D_{fat}^{1064 nm}}{D_{tumor}^{1064 nm}} = 4.4, \text{ and}$$

$$\frac{D_{tumor}^{1064 nm}}{D_{tumor}^{532 nm}} = 8,$$

$$\frac{D_{fat}^{532 nm}}{D_{tumor}^{532 nm}} = 17.51.$$

Similar results are obtained using the integral in time $[D=\int D(t)dt]$ of $D(t)$ as $D$ (instead of the peak value) or using Eq. 1 to calculate $D$ the integral in time of $I(t)$ in the parallel and perpendicular polarization orientation $[I_{para}=\int I_{para}(t)dt$ and $I_{perp}=\int I_{perp}(t)dt]$. The different values of the degree of polarization preservation of the propagating light for different laser wavelengths shows that, in an imaging system based on polarization preservation, use of different laser wavelengths provides a means for characterizing a tissue being tested and a means for helping in imaging the tissue. For example, it is possible to determine if a tumor is benign or malignant by imaging the tissue under investigation using different laser wavelengths. This information can then be used to generate a pseudocolor spatial map where, for example, a malignant tumor has a different color than a benign tumor.

Using optical imaging based on polarization spectral-time gating in accordance with the teachings of the present invention has many advantages over other modalities like X-rays, MRI and ultrasound, which cannot distinguish between malignant tumors and benign tumors. This advantage arises from the fact that the recorded signal, in addition to possessing information regarding the imaging details, contains information on the interaction of the light at different wavelengths with the tissue. Consequently, the present technique adds a new dimension to the existing state of image formation. A polarization spatial map can be formed in accordance with the teachings of the present invention by measuring $D(R)$ at different positions R either point by point or using CCD image mapping. Polarization gating according to the present invention can also be combined with time and space gating to enhance image resolution and contrast.

Referring now to FIG. 6, there is shown a schematic view of a second embodiment constructed according to the teachings of the present invention of an apparatus for imaging and/or characterizing a tissue, the apparatus being represented generally by reference numeral 71.

Apparatus 71 includes a polarizer 73, which ensures polarized incident light, and a polarizer/analyzer 75, which, depending upon its orientation, is used to discriminate the two polarization components of the emergent light from the sample S. Apparatus 71 also includes an imaging system 77, which is used to obtain the images from the two polarization components. Finally, one- or two- or three-dimensional mapping of the sample is obtained using appropriate electronics and computer software 79 to estimate and image the degree of polarization (D or d or p) of the emergent light.

Referring now to FIG. 7, there is shown a schematic view of a third embodiment constructed according to the teachings of the present invention of an apparatus for imaging and/or characterizing a tissue, the apparatus being represented generally by reference numeral 81.

Apparatus 81 includes a polarizer 83, which is used to ensure that polarized light is transmitted to a sample S, a time and/or spatial gate 85 (e.g., Kerr gate or parametric gate or electronic gate and/or 4F Fourier spatial gate or another equivalent gating device), which is used to select only early-arriving and forwardly-propagating photons of the emergent light from sample S, a polarizer/analyzer 87, which, depending upon its orientation, is used to discriminate the two polarization components of the emergent, gated light, and an imaging system 89, which is used to obtain the images from the two polarization components. Apparatus 81 also includes electronics and computer software 90, which is used to estimate and image the degree of polarization (D or d or p) of the emergent light.

Referring now to 8, there is a schematic view of a fourth embodiment constructed according to the teachings of the present invention of an apparatus for imaging and/or characterizing a tissue, the apparatus being represented generally by reference numeral 91.

Apparatus 91 includes a polarizer 93, which is used to ensure that polarized light is transmitted to a sample S, a polarizer/analyzer 95, which, depending upon its orientation, is used to discriminate the two polarization components of the emergent light from sample S, a time and/or spatial gate 97 (e.g., Kerr gate or parametric gate or electronic gate and/or 4F Fourier spatial gate or another equivalent gating device), which is used to select only early-arriving and forwardly-propagating photons of the emergent light from analyzer 95, and an imaging system 99, which is used to obtain the images from the two polarization components. Apparatus 91 also includes electronics and computer software 100, which is used to estimate and image the degree of polarization (D or d or p) of the emergent light.

Referring now to FIG. 9, there is a schematic view of a fifth embodiment constructed according to the teachings of the present invention of an apparatus for imaging and/or characterizing a tissue, the apparatus being represented generally by reference numeral 101.

Apparatus 101 includes a polarizer 103, which is used to ensure that polarized light is transmitted to a sample S, a polarizer/analyzer 105, which, depending upon its orientation, is used to discriminate the two polarization components of the emergent light from sample S, an image intensifier 107, which is time gated and is appropriately triggered to allow only the early part of the emergent light from analyzer 105 to be amplified, and a CCD imaging system 109, which is used to obtain the images from the two polarization components. Apparatus 101 also includes electronics and computer software 110, which is used to estimate and image the degree of polarization (D or d or p) of the emergent light.

Referring now to FIG. 10, there is a schematic view of a sixth embodiment constructed according to the teachings of the present invention of an apparatus for imaging and/or characterizing a tissue, the apparatus being represented generally by reference numeral 111.

Apparatus 111 includes a polarizer 113, which is used to ensure that polarized light is transmitted to a sample S, a polarizer/analyzer 115, which, depending upon its orientation, is used to discriminate the two polarization components of the emergent light from sample S, a 4F Fourier space gate 116, which is used to reduce the diffusive component of the emergent light, an image intensifier 117, which is time gated and is appropriately triggered to allow only the early part of the emergent light from gate 116 to be amplified, and a CCD imaging system 119, which is used to obtain the images from the two polarization components. Apparatus 111 also includes electronics and computer software 120, which is used to estimate and image the degree of polarization (D or d or p) of the emergent light.

Referring now to FIG. 11, there is shown a schematic view of one type of combination 121 analyzer and imaging system adapted for use in the systems described above. In the embodiment shown in FIG. 11, the incident polarization is linear, analyzer 123 comprising a linear polarizer, whose orientation may be altered by mechanical or electrooptical means so that the two polarization image components of the emergent light (i.e., parallel and perpendicular to the incident light polarization) are recorded at different times by the imaging unit 125.

Referring now to FIG. 12, there is shown a schematic view of an alternative combination 131 to that shown in FIG. 11. In the embodiment of FIG. 12, the incident polarization is circular (elliptical), analyzer 133 comprising a retardation plate 135 ($\lambda/4$ for circular polarization) and a linear polarizer 137 with orientation that may be altered via mechanical or electrooptical means at $\pm 45°$ with respect to the o-axis of retardation plate 133 so that the two polarization image components of the emergent light (left-hand and right-hand circular) are recorded at different times by imaging unit 139.

Referring now to FIG. 13, there is shown a schematic view of another alternative combination 141 to that shown in FIG. 11. In the embodiment of FIG. 13, the incident polarization is linear, the analyzer comprising a polarizing beam splitter 143 so that the two polarization image components of the emergent light (parallel and perpendicular to the incident light polarization) are recorded simultaneously by two imaging units 145 and 147.

Referring now to FIG. 14, there is shown a schematic view of yet another alternative combination 151 to that shown in FIG. 11. In the embodiment of FIG. 14, the incident polarization is circular (elliptical), the analyzer comprising a retardation plate 153 ($\lambda/4$ for circular polarization) and a polarizing beam splitter 155 with axis at $\pm 45°$ with respect to the o-axis of retardation plate 153 so that the two polarization image components of the emerged light (parallel and perpendicular to the incident light polarization) are recorded simultaneously by imaging units 157 and 159.

Referring now to FIG. 15, there is shown a schematic view of a seventh embodiment constructed according to the teachings of the present invention of an apparatus for imaging and/or characterizing a tissue, the apparatus being represented generally by reference numeral 161.

Apparatus 161 includes a light source for producing a light beam. The light beam is collimated and then polarized using a polarizer. The beam propagates through the sample. The emerged light is collected by appropriate optical elements (lenses and/or mirrors) and directed into a point detector (e.g., photodiode, photomultiplier) after passing through an analyzer and a time and/or spatial gate. The apparatus is mounted on a table accommodating x-y-z and/or $\theta$-r-z translational/rotational stages that allow one to scan the sample to obtain a point by point mapping. Apparatus 161 also includes electronics and computer software (not shown), which is used to estimate and image the degree of polarization (D or d or p) of the emergent light.

Referring now to FIG. 16, there is shown a schematic view of an eighth embodiment constructed according to the teachings of the present invention of an apparatus for imaging and/or characterizing a tissue, the apparatus being represented generally by reference numeral 171.

Apparatus 171 includes a light source for producing a light beam. The light beam is collimated and polarized using a polarizer. The beam propagates the sample. The emergent light is collected by appropriate optical elements (lenses and/or mirrors) and directed into a fast point detector (photodiode, photomultiplier) after passing through the analyzer. The apparatus is mounted on a table accommodating x-y-z and/or $\theta$-r-z translational/rotational stages that allow one to scan the sample to obtain a point by point mapping. The signal of the fast photodetector is amplified and directed into the input of a sampling oscilloscope where the signal is time-gated to selectively obtain the intensity of the early part of emergent light. Using a lock-in amplifier or a boxcar integrator, the sensitivity of the system can be improved (if needed) and the time-gated signal is sent to a computer for image processing.

Referring now to FIG. 17, there is shown a schematic view of a ninth embodiment constructed according to the teachings of the present invention of an apparatus for imaging and/or characterizing a tissue, the apparatus being represented generally by reference numeral 181.

Apparatus 181 includes a light source for producing a light beam. The light beam is collimated and polarized using a polarizer. A beam deflector is used to scan the sample in the y-z plane. The beam propagates the sample. The emergent light is collected by a beam collector scanning in the y-z plane in phase with the beam deflector and directed into a point detector (photodiode, photomultiplier) after passing through the analyzer and the time and/or spatial gate. The deflector with the in-phase beam collector allow scanning of the sample to obtain a point by point mapping. Appartus 181 also includes electronics and computer software (not shown), which is used to estimate and image the degree of polarization (D or d or p) of the emergent light.

Referring now to FIG. 18, there is shown a schematic view of a tenth embodiment constructed according to the teachings of the present invention of an apparatus for imaging and/or characterizing a tissue, the apparatus being represented generally by reference numeral 191.

Apparatus 191 includes a light source for producing a light beam. The light beam is collimated and polarized using a polarizer. A beam deflector is used to scan the sample in the y-z plane. The beam propagates the sample. The emergent light is collected by a beam collector scanning in the y-z plane in phase with the beam deflector and directed into a fast point photodetector (photodiode, photomultiplier) after passing through the analyzer. The signal of the fast photodetector is amplified and directed into the input of a sampling oscilloscope where the signal is time-gated to selectively obtain the intensity of the early part of emergent light. Using a lock-in amplifier or a boxcar integrator, the sensitivity of the system can be improved (if needed) and the time-gated signal is sent to a computer for image processing. The deflector with the in-phase beam collector allow scanning of the sample to obtain a point by point mapping.

Referring now to FIG. 19, there is shown a schematic view of an eleventh embodiment constructed according to the teachings of the present invention of an apparatus for imaging and/or characterizing a tissue, the apparatus being represented generally by reference numeral 201.

Apparatus 201 includes a light source for producing a light beam. The light beam is collimated and polarized using a polarizer. The beam propagates the sample. The emergent light is collected by appropriate optical elements (lenses and/or mirrors) and directed into an array detector after passing through the analyzer and the time and/or spatial gate. The apparatus is mounted on a table accommodating x-y-z and/or $\theta$-r-z translational/rotational stages that allow one to scan the sample to obtain a point by point mapping. Appartus 201 also includes electronics and computer software (not shown), which is used to estimate and image the degree of polarization (D or d or p) of the emergent light.

Referring now to FIG. 20, there is shown a schematic view of a twelfth embodiment constructed according to the teachings of the present invention of an apparatus for imaging and/or characterizing a tissue, the apparatus being represented generally by reference numeral 211.

Apparatus 211 includes a light source for producing a light beam. The light beam is collimated and polarized using a polarizer. The beam propagates the sample. The emergent light is collected by appropriate optical elements (lenses and/or mirrors) and after passing through the analyzer and the time and/or spatial gate is directed into a two-dimensional detector to record a shadowgram. The apparatus is mounted on a table accommodating x-y-z and/or θ-r-z translational/rotational stages that allow one to scan the sample. Appartus 211 also includes electronics and computer software (not shown), which is used to estimate and image the degree of polarization (D or d or p) of the emergent light.

Referring now to FIG. 21, there is shown a schematic view of a thirteenth embodiment constructed according to the teachings of the present invention of an apparatus for imaging and/or characterizing a tissue, the apparatus being represented generally by reference numeral 221.

Apparatus 221 includes a light source for producing a light beam. The light beam is collimated, expanded and polarized using a polarizer. The beam propagates the sample. The emergent light is collected by appropriate optical elements (lenses and/or mirrors) and after passing through the analyzer and the time and/or spatial gate is directed into a two-dimensional detector to record a shadowgram. The apparatus is mounted on a table accommodating x-y-z and/or θ-r-z translational/rotational stages that allow one to scan the sample. Appartus 221 also includes electronics and computer software (not shown), which is used to estimate and image the degree of polarization (D or d or p) of the emergent light.

Referring now to FIGS. 22(a) and 22(b), there can be seen the temporal profiles of the degree of polarization of the emergent light under 1064 nm laser pulsed illumination of human breast tissue in the case of (a) 3 mm fat and cancer tumor tissue samples obtained from a patient; and (b) 3.3 mm fat and glandular tissue samples obtained from the same patient, respectively. FIGS. 22(a) and 22(b) demonstrate that cancer tumor tissue depolarizes light faster than does normal tissue.

Referring now to FIG. 23, there can be seen a graphic representation of the degree of polarization in the transverse position of 532 nm laser light transmitted through 3 mm thick breast tissue sample containing a cancerous tumor section. The 532 nm laser beam was expanded to illuminate the sample. The part of the sample containing the cancer tumor depolarizes almost completely the 532 nm light while light propagating through the fat tissue is partially polarized. The profile clearly distinguishes the cancerous part of the sample from the normal part of the sample.

An imaging system based on the present discovery of differential polarization preservation of propagating light through turbid media should make use of the following considerations:

(1) The incident light should be polarized. Accordingly, the light source can be any laser available or any other pulsed or continuous light source which provides polarized light with or without the use of a polarizing element. The operating wavelength range is preferably 400–1600 nm.

(2) The two polarization components of the output light (parallel and perpendicular to the incident polarization) are recorded. From these components the degree of polarization preservation of the output light is calculated. Accordingly, the two polarization components can be measured simultaneously (using for example a polarizing beam-spliter and two detectors) or at different times (using one photodetector and an analyzer that can change its polarization orientation or by changing the input polarization and leaving the analyzer at the same position).

(3) An image is obtained by recording the degree of polarization of the output light propagating through the scattering medium point by point or through mapping. Accordingly, a suitable detector currently available is a cooled CCD. The two images of the parallel and perpendicular polarization components of the propagating light are recorded and via interimage operation involving these components an image of the degree of polarization is obtained.

(4) Changing the wavelength of the input light, the image of the degree of polarization changes with respect to the relative intensity of the observed types of tissues (tumor, fat, etc.). By recording the dependence of the changes of the image as a function of the incident wavelength, a pseudo-colored image can be generated containing additional information on the types of tissues observed (e.g. separating benign from malignant tumors). The polarized light source utilized can be monochromatic or containing a band of frequencies. The degree of polarization image at various wavelengths can be obtained by a) varying the wavelength (for monochromatic light), b) varying the central wavelength or c) varying the bandwidth (for a band of frequencies).

(5) The polarization preservation imaging technique can be combined with other techniques that provide selection of the photons propagated in the forward direction. Fourier space gate and/or Kerr gate or gates based on picosecond optical or electronic switches can be combined with the polarization imaging system for enhanced image resolution.

The following observations, among others, may be made about the present invention:

1. The polarization preservation in tissues and random media can be used for time gating the early part of the output pulse;

2. Use polarized light of different wavelength and changing state of polarization for tissue diagnosis to separate cancer, benign, fat and normal tissue;

3. The temporal profile resulting from the subtraction of the components of the output pulse parallel and perpendicular to the incident polarization extents up to 100 ps after the arrival of the ballistic component;

4. The time gate obtained through the polarization preservation opens with the arrival of the ballistic light up to about 100 ps after the arrival of the ballistic light;

5. Polarization preservation can be used for selective collection of the light propagating in the forward direction in human tissues;

6. The degree of polarization preservation of light propagating in human tissue is different depending on the type of tissue (fat, glandular, tumors or cysts);

7. The degree of polarization of light that propagate through tissue depends on the wavelength of the propagating light and tissue type;

8. The change of the degree of polarization as a function of the wavelength of the propagating light depends on the type of the tissue;

9. The change of the degree of polarization as a function of the wavelength of the propagating light can be used for obtaining information on the type of the tissue under investigation;

10. The degree of polarization of the propagating light can be measured by any function containing the parallel ($I_{parallel}$) and perpendicular ($I_{perpendicular}$) components of the output light such as eq. 1, $[I_{para}-I_{perp}]$, $[I_{para}/I_{perp}]$ and $[I_{perp}/(I_{para}+I_{perp})]$;

11. The degree of polarization of the propagating light can be measured using the integral in time of D(t) (instead of the peak value) or using the integral in time of $I(t)_{parallel}$ and $I(t)_{perpendicular}$ in combination with paragraph 10 above;

12. Polarization preservation can be used for imaging in human tissue point by point or over area;

13. A map of D(R) can be used for imaging;

14. The polarization spatial time gate D(R,t) can be used in combination with Fourier space gate and time gate (optical or electronic gate);

15. A $\Delta D(R,\lambda)$ map can be used for imaging minors and allow for the differentiation of malignant from benign tumors;

16. Use a combination of $D(\lambda,t,R)$ and/or $\Delta D(R,\lambda)$ map with Fourier gating for imaging in tissues;

17. A combination of $D(\lambda,t,R)$ and/or $\Delta D(R,\lambda)$ map with any time gating technique selecting the forwardly propagating photons (ballistic and snake part of the output pulse) such as Kerr gate or gates based on picosecond optical or electronic swishes and electronic time gates can be used for enhanced image resolution;

18. Optical tomography and mammography can be achieved using the following principals: a) the polarization preservation of initially polarized light propagating in tissues, b) the dependence of the degree of polarization on the wavelength of the propagating light, and c) the mapping dependence of the degree of polarization of the output light to the type of tissue (fat, glandular, tumors, cysts);

19. The polarized light sources required for use with the polarization preservation technique can be pulsed or continuous, laser source or any other light source operating in the spectral region between 400 and 1600 nm such as Ti:Sapphire laser (800–1000 nm), Cr4+:Forsterite laser (1100–1300 nm) or Cr4+:YAG (1300–1600 nm). The only requirement is polarized incident light; and 20. The preservation of the polarization of light propagating in human tissue is a property with great importance in the field of optical tomography and mammography. The initially polarized light propagating through the tissue retains some of the information concerning its initial polarization. The degree of polarization of the output light depends on the wavelength of the light and the type of the tissue (glandular, fat, cyst or minor). The polarization preservation technique can be used as a 100 ps time gate and as a tool for optical imaging and characterization of the type of tissue for diagnostic reasons. The polarization preservation imaging technique can be combined with other time-gated imaging techniques for enhanced image clarity and volume of information.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for imaging an object located in or behind a human breast tissue sample, said method comprising the steps of:
   (a) illuminating the object through the human breast tissue sample with a pulse of light, the pulse of light having a wavelength selected from the group consisting of 532 nm and 1064 nm, being polarized and having an initial state of polarization, whereby light consisting of a ballistic component, a snake-like component and a diffuse component emerges from the illuminated human breast tissue sample;
   (b) passing the emergent light from the illuminated human breast tissue sample through a polarizing means oriented parallel to the initial state of polarization of said pulse of light to preferentially select said ballistic component and said snake-like component; and
   (c) forming an image of the light passed through said polarizing means.

2. The method as claimed in claim 1 wherein the initial state of polarization of the pulse of light is linear.

3. The method as claimed in claim 1 wherein the initial state of polarization of the pulse of light is elliptical.

4. A method for imaging an object located in or behind a turbid medium, said method comprising the steps of:
   (a) providing a beam of light;
   (b) polarizing the beam of light, whereby the beam of light has an initial state of polarization;
   (c) illuminating the object through the turbid medium with the polarized beam of light, whereby light consisting of a ballistic component, a snake-like component and a diffuse component emerges from the illuminated turbid medium;
   (d) detecting the degree of polarization of the emergent light to determine the extent to which the emergent light includes the ballistic and snake-like components; and
   (e) forming an image of the object using the detected light.

5. The method as claimed in claim 4 wherein said detecting step comprises passing the emergent light through polarizing means.

6. The method as claimed in claim 5 wherein said polarizing means includes a retardation plate and a linear polarizer.

7. The method as claimed in claim 4 wherein said detecting step comprises detecting light point by point or over an area using photomultiplier or photocathode or CCD camera or other equivalent photodetector.

8. The method as claimed in claim 4 wherein said beam of light is a pulse of light.

9. The method as claimed in claim 4 wherein said beam of light is provided by means of a continuous light source.

10. A method for imaging an object located in or behind a turbid medium, said method comprising the steps of:
    (a) illuminating the object through the turbid medium with a pulse of light, the pulse of light being passed through a polarizer and having an initial state of polarization, whereby light consisting of a ballistic component, a snake-like component and a diffuse component emerges from the illuminated turbid medium;
    (b) passing the emergent light from the illuminated turbid medium through an analyzer appropriately oriented relative to said polarizer so as to alternately transmit light of two polarization states;
    (c) collecting the emerged light in the two polarization states to measure the emerged polarized light which belongs to the ballistic and snake-like components; and
    (d) forming an image of the degree of polarization D of the emerged light.

11. The method as claimed in claim 10 wherein the degree of polarization D is measured by a function containing the two polarization components $I_a$ and $I_b$ of the emergent light, such as $d(t)=I_a(t)-I_b(t)$, $p(t)=I_a(t)/I_b(t)$, $D(t)=[I_a(t)-I_b(t)]/[I_a(t)+I_b(t)]$ or $D'(t)=[I_b(t)]/[I_a(t)-I_b(t)]$.

12. The method as claimed in claim 11 wherein the degree of polarization D is the peak value of D(t).

13. The method as claimed in claim 11 wherein the degree of polarization D is the averaged integral in time value of D(t).

14. The method as claimed in claim 11 wherein the degree of polarization is obtained using the averaged integral in time value of the two polarization components of the emerged light.

15. The method as claimed in claim 11 wherein the emergent light is time-gated using appropriate time-gating apparatus.

16. The method as claimed in claim 11 wherein the emergent light is passed through a spatial gate, such as a 4F Fourier spatial gate.

17. The method as claimed in claim 11 wherein subtraction of the two polarization components of the emergent light is equivalent to a time gate of less than 100 ps in time duration following the arrival of the ballistic component.

18. The method as claimed in claim 11 wherein the image is recorded in two or three dimensional map of D(R,t) or D(R) wherein R is the spatial coordinate in the sample and t is time, describing the dependence of the degree of polarization of the emergent light from different parts of the tissue D(R) and the time profile of the degree of polarization D(t).

19. The method as claimed in claim 11 wherein the pulse of light has a wavelength selected from the group consisting of 532 nm and 1064 nm.

20. A method for imaging a tissue and for identifying the tissue, said method comprising the steps of:

(a) illuminating the tissue with a first pulse of light passing through a polarizer, the first pulse of light having an initial state of polarization, whereby light from the first pulse consisting of a ballistic component, a snake-like component and a diffuse component emerges from the illuminated tissue;

(b) passing the light from the first pulse emergent from the illuminated tissue through an analyzer appropriately oriented relative to said polarizer so as to alternately transmit light of two polarization states;

(c) forming an image of the degree of polarization of the emergent light from the first pulse;

(d) illuminating the tissue with a second pulse of light having a different wavelength than the first pulse, the second pulse of light passing through a polarizer and having an initial state of polarization, whereby light from the second pulse consisting of a ballistic component, a snake-like component and a diffuse component emerges from the illuminated tissue;

(e) passing the light from the second pulse emergent from the illuminated tissue through an analyzer appropriately oriented relative to said polarizer so as to alternately transmit light of two polarization states;

(f) forming an image of the degree of polarization of the emergent light from the second pulse;

(g) repeating steps (d) through (f) if required; and (h) forming an image of the tissue, said image containing information regarding the type of tissue using the images formed in steps (c) and (f).

21. The method as claimed in claim 20 wherein the tissue sample is a human brain tissue sample.

22. The method as claimed in claim 20 wherein the pulse of light is a laser pulse of light generated by a laser selected from the group consisting of Ti:Sapphire, $Cr^{4+}$:Forsterite, $Cr^{4+}$:YAG, Nd:YAG and semiconductor diode lasers.

23. The method as claimed in claim 20 wherein the pulse of light is replaced with a continuous monochromatic light source from a lamp or laser.

24. The method as claimed in claim 20 wherein the pulse of light is replaced with a continuous non-monochromatic light source.

25. The method as claimed in claim 23 wherein the different wavelengths of the first and second pulses are measured from the central wavelength of the band of frequencies utilized.

26. The method as claimed in claim 24 wherein the different wavelengths of the first and second pulses are measured from the bandwidth of the band of frequencies utilized.

27. The method as claimed in claim 20 wherein the polarization of the illuminating light pulse is linear and the two states of polarization of the emergent light is parallel and perpendicular to the incident light pulse polarization.

28. The method as claimed in claim 20 wherein the polarization is circular and the two states of polarization of the emergent light is right-hand and left-hand circularly polarized.

29. The method as claimed in claim 20 wherein the polarizer comprises appropriate optical elements to define the polarization state of the illuminating light.

30. The method as claimed in claim 28 wherein the polarizer comprises a retardation plate and linear polarizer.

31. The method as claimed in claim 20 wherein the imaging is performed point by point or over area using photomultiplier or photodiode or CCD camera.

32. The method as claimed in claim 20 wherein the degree of polarization D is measured by a function containing the two polarization components $I_a$ and $I_b$ of the emergent light, such as $d(t)=I_a(t)-I_b(t)$, $p(t)=I_a(t)/I_b(t)$, $D(t)=[I_a(t)-I_b(t)]/[I_a(t)+I_b(t)]$ or $D'(t)=[I_b(t)]/[I_a(t)-I_b(t)]$.

33. The method as claimed in claim 32 wherein the degree of polarization D is the peak value of D(t).

34. The method as claimed in claim 32 wherein the degree of polarization D is the averaged integral in time value of D(t).

35. The method as claimed in claim 32 wherein the degree of polarization is obtained using the averaged integral in time value of the two polarization components of the emerged light.

36. The method as claimed in claim 20 wherein the emergent light is time-gated using appropriate time-gating apparatus.

37. The method as claimed in claim 20 wherein the emergent light is passed through a spatial gate, such as a 4F Fourier spatial gate.

38. The method as claimed in claim 20 wherein the image containing the information regarding the type of tissue is obtained utilizing the different degree of polarization that different types of tissues exhibit at different wavelengths.

39. The method as claimed in claim 20 wherein the image containing the information regarding the type of tissue is recorded in a two or three dimensional map of D(R,t,λ) or D(R) wherein R is the spatial coordinate in the sample, t is time and λ is wavelength, describing the dependence of the degree of polarization of the emergent light from different parts of the tissue D(R), the time profile of the degree of polarization D(t) and the dependence of the degree of polarization in the wavelength of the illuminating light D(λ).

40. The method as claimed in claim 20 wherein the image containing the information regarding the type of tissue is recorded in a two or three dimensional map of D(R,λ) describing the dependence of the degree of polarization of the emergent light from different parts of the tissue D(R) and the dependence of the degree of polarization in the wavelength of the illuminating light D(λ).

41. The method as claimed in claim 20 wherein the selection of different wavelengths is based on the wavelength of absorption peaks and minima of the tissue under investigation arising from $H_2O$ and/or fat to highlight tumors.

42. A method for imaging an object located in or behind a turbid medium, said method comprising the steps of:
(a) illuminating the object through the turbid medium with a first pulse of light, the first pulse of light being polarized and having an initial state of polarization, whereby light from the first pulse consisting of a ballistic component, a snake-like component and a diffuse component emerges from the illuminated turbid medium;
(b) passing the light from the first pulse emergent from the illuminated turbid medium through one of a polarizer oriented parallel to the initial state of polarization of said first pulse of light and an analyzer oriented perpendicular to the initial state of polarization of said first pulse of light;
(c) detecting the light from the first pulse passed through one of said polarizer and said analyzer;
(d) illuminating the object through the turbid medium with a second pulse of light, the second pulse of light being polarized in an initial state parallel to that of said first pulse of light, whereby light from the second pulse consisting of a ballistic component, a snake-like component and a diffuse component emerges from the illuminated turbid medium;
(e) passing the light from the second pulse emergent from the illuminated turbid medium through the other of said polarizer and said analyzer;
(f) detecting the light from the second pulse passed through the other of said polarizer and said analyzer; and
(g) forming an image of the object in or behind the turbid medium using the light detected in steps (c) and (f).

43. The method as claimed in claim 42 wherein the turbid medium is a tissue sample.

44. The method as claimed in claim 43 wherein the tissue sample is a human tissue sample.

45. The method as claimed in claim 44 wherein the tissue sample is a human breast tissue sample.

46. The method as claimed in claim 42 wherein the pulse of light is a pulse of laser light.

47. The method as claimed in claim 42 wherein the pulse of light has a wavelength in the spectral region between 400 and 1600 nm.

48. The method as claimed in claim 47 wherein the pulse of light has a wavelength selected from the group consisting of 532 nm and 1064 nm.

49. A method for identifying a tissue, said method comprising the steps of:
(a) illuminating the tissue with a pulse of light, the pulse of light being polarized and having an initial state of polarization, whereby light consisting of a ballistic component, a snake-like component and a diffuse component emerges from the illuminated tissue;
(b) passing the emergent light from the illuminated tissue through one of a polarizer oriented consistent with the initial state of polarization of said pulse of light and an analyzer oriented opposite to the initial state of polarization of said pulse of light;
(c) detecting the light passed through one of said polarizer and said analyzer; and
(d) comparing the detected light to appropriate standards so as to identify the type of tissue tested.

50. The method as claimed in claim 49 wherein said passing step comprising passing the emergent light through a polarizer oriented consistent with the initial state of polarization of said pulse of light.

51. The method as claimed in claim 49 wherein said passing step comprising passing the emergent light through an analyzer oriented opposite to the initial state of polarization of said pulse of light.

52. The method as claimed in claim 49 wherein the tissue is a human tissue.

53. The method as claimed in claim 52 wherein the tissue is a human breast tissue.

54. The method as claimed in claim 49 wherein the pulse of light is a pulse of laser light.

55. The method as claimed in claim 49 wherein the pulse of light has a wavelength in the spectral region between 400 and 1600 nm.

56. The method as claimed in claim 55 wherein the pulse of light has a wavelength selected from the group consisting of 532 nm and 1064 nm.

57. An apparatus for imaging an object in a turbid medium, the apparatus comprising:
(a) means for illuminating an object in a turbid medium from a first side thereof with light, said light being polarized and having an initial state of polarization, whereby light consisting of a ballistic component, a snake-like component and a diffuse component emerges from the turbid medium;
(b) polarization means for alternately passing the parallel and perpendicular components of the light emergent from the turbid medium;
(c) means for detecting the parallel and perpendicular components of the emergent light;
(d) means for calculating one of a ratio and a difference of the parallel and perpendicular components of the emergent light;
(e) means for forming an image of the object in the turbid medium using said one of said ratio and said difference.

58. The apparatus as claimed in claim 57 further comprising means, located between said detecting means and the turbid medium for time and/or space gating the light emergent from the turbid medium.

59. An apparatus for imaging an object in a turbid medium, the apparatus comprising:
(a) a light source for emitting a beam of light towards the turbid medium;
(b) means for polarizing the beam of light prior to illuminating the turbid medium;
(c) analyzing means for selectively passing the light emergent from the turbid medium based upon its polarization;
(d) means for detecting the analyzed light; and
(e) means for generating a one or two or three dimensional map of the degree of polarization (D or d or p) of the emerged light.

60. The apparatus as claimed in claim 59 further comprising a time and/or space gate disposed between the turbid medium and the analyzing means.

61. The apparatus as claimed in claim 59 further comprising a time and/or space gate disposed between the analyzing means and the detecting means.

62. The apparatus as claimed in claim 59 further comprising a movable mounting table upon which the light source, polarizing means, analyzing means and detecting means are mounted.

* * * * *